US 10,941,373 B2

(12) United States Patent
Kim et al.

(10) Patent No.: US 10,941,373 B2
(45) Date of Patent: Mar. 9, 2021

(54) CULTURE MEDIUM STERILIZED FOR MICROALGAE HIGH DENSITY CULTURE, AND THE AIR COMPRESSION, AIR COOLING, CARBON DIOXIDE AUTOMATICALLY SUPPLIED, SEALED VERTICAL PHOTOBIOREACTOR, HARVESTING, DRYING APPARATUS AND CHARACTERIZED IN THAT TO PROVIDE A CARBON DIOXIDE BIOMASS CONVERSION FIXED, AIR AND WATER PURIFICATION METHOD USING THE SAME

(71) Applicant: GREENTECH VENTURES, INC., Chantilly, VA (US)

(72) Inventors: Young Nam Kim, Gyeonggi-do (KR); Yong Woo Park, Gyeonggi-do (KR)

(73) Assignee: GREENTECH VENTURES, INC., Chantilly, VA (US)

( * ) Notice: Subject to any disclaimer, the term of this patent is extended or adjusted under 35 U.S.C. 154(b) by 229 days.

(21) Appl. No.: 16/047,683

(22) Filed: Jul. 27, 2018

(65) Prior Publication Data
US 2019/0040347 A1 Feb. 7, 2019

Related U.S. Application Data

(63) Continuation-in-part of application No. PCT/US2017/040760, filed on Jul. 5, 2017.

(30) Foreign Application Priority Data

Jul. 5, 2016 (KR) .................. 10-2016-0084680

(51) Int. Cl.
*C12M 1/00* (2006.01)
*C12M 1/12* (2006.01)
(Continued)

(52) U.S. Cl.
CPC ............. *C12M 21/02* (2013.01); *B01D 53/84* (2013.01); *C02F 3/322* (2013.01); *C12M 23/18* (2013.01);
(Continued)

(58) Field of Classification Search
None
See application file for complete search history.

(56) References Cited

U.S. PATENT DOCUMENTS 5,659,977 A * 8/1997 Jensen ................ F02G 5/02
34/547
9,243,219 B2 1/2016 Dimitrelos
(Continued)

FOREIGN PATENT DOCUMENTS

CL 199903150 1/2001
KR 20120052438 A 5/2012
(Continued)

OTHER PUBLICATIONS

Algae4f, Co., Inc., "High quality natural bio-chlorella eco-friendly organic agricultural materials," For HumanNature Brochure, Apr. 2018, 41 pages, Algae4f, Inc., Goyang-si, Republic of Korea (with English Translation).
(Continued)

*Primary Examiner* — Holly Kipouros
(74) *Attorney, Agent, or Firm* — Potomac Law Group, PLLC

(57) ABSTRACT

A microalgae culture broth producing system includes a device for culture broth sterilization using a micro bubble generator, an air compression and pressure equalization device for the injection of carbon dioxide and oxygen in the atmosphere into the culture broth. The system also includes an air chilling device to maintain suitable culture broth temperature when water temperature is too high, an auto-
(Continued)

matic carbon dioxide supply device to promote photosynthesis, and a sealed vertical photobioreactor to block out pollutants and increase dissolved carbon dioxide and oxygen concentration. The system further includes a high-efficiency harvesting device using hollow fiber membranes, and a hot air drying device using the waste heat generated by air compression.

7 Claims, 18 Drawing Sheets

(51) Int. Cl.
*C12M 1/36* (2006.01)
*B01D 53/84* (2006.01)
*C02F 3/32* (2006.01)
*C12M 1/26* (2006.01)
*C12M 1/34* (2006.01)
*C02F 1/78* (2006.01)
*C02F 101/10* (2006.01)
*C02F 101/16* (2006.01)

(52) U.S. Cl.
CPC ............ *C12M 25/10* (2013.01); *C12M 31/00* (2013.01); *C12M 33/14* (2013.01); *C12M 37/00* (2013.01); *C12M 39/00* (2013.01); *C12M 41/06* (2013.01); *C12M 41/12* (2013.01); *C12M 41/26* (2013.01); *C12M 41/40* (2013.01); *C12M 41/48* (2013.01); *C12M 47/14* (2013.01); *C02F 2101/105* (2013.01); *C02F 2101/16* (2013.01)

(56) References Cited

U.S. PATENT DOCUMENTS

| 9,386,774 B2 | 7/2016 | Shinde et al. |
| 2012/0315692 A1 | 12/2012 | Hu et al. |
| 2015/0232802 A1 | 8/2015 | Ganuza et al. |
| 2016/0165895 A1 | 6/2016 | Shinde et al. |
| 2016/0166985 A1 | 6/2016 | Lau et al. |

FOREIGN PATENT DOCUMENTS

| KR | 101423285 B1 | 7/2014 |
| KR | 20150065286 A | 6/2015 |
| KR | 20160057903 A | 5/2016 |
| KR | 20160088265 A | 7/2016 |
| KR | 101738872 B1 | 5/2017 |
| WO | 2008079724 A2 | 7/2008 |
| WO | 2014133793 A1 | 9/2014 |
| WO | 2016089104 A1 | 6/2016 |
| WO | 2016100550 A1 | 6/2016 |
| WO | 2017044774 A1 | 3/2017 |
| WO | 2017218896 A1 | 12/2017 |
| WO | 2018039569 A1 | 3/2018 |
| WO | 2018052502 A1 | 3/2018 |
| WO | 2018053211 A1 | 3/2018 |
| WO | 2018110888 A1 | 6/2018 |

OTHER PUBLICATIONS

Extended European Search Report dated Jan. 7, 2020 for European Patent Application No. 17824832.4.
International Search Report dated Oct. 18, 2017, in International Application No. PCT/US2017/040760.

* cited by examiner

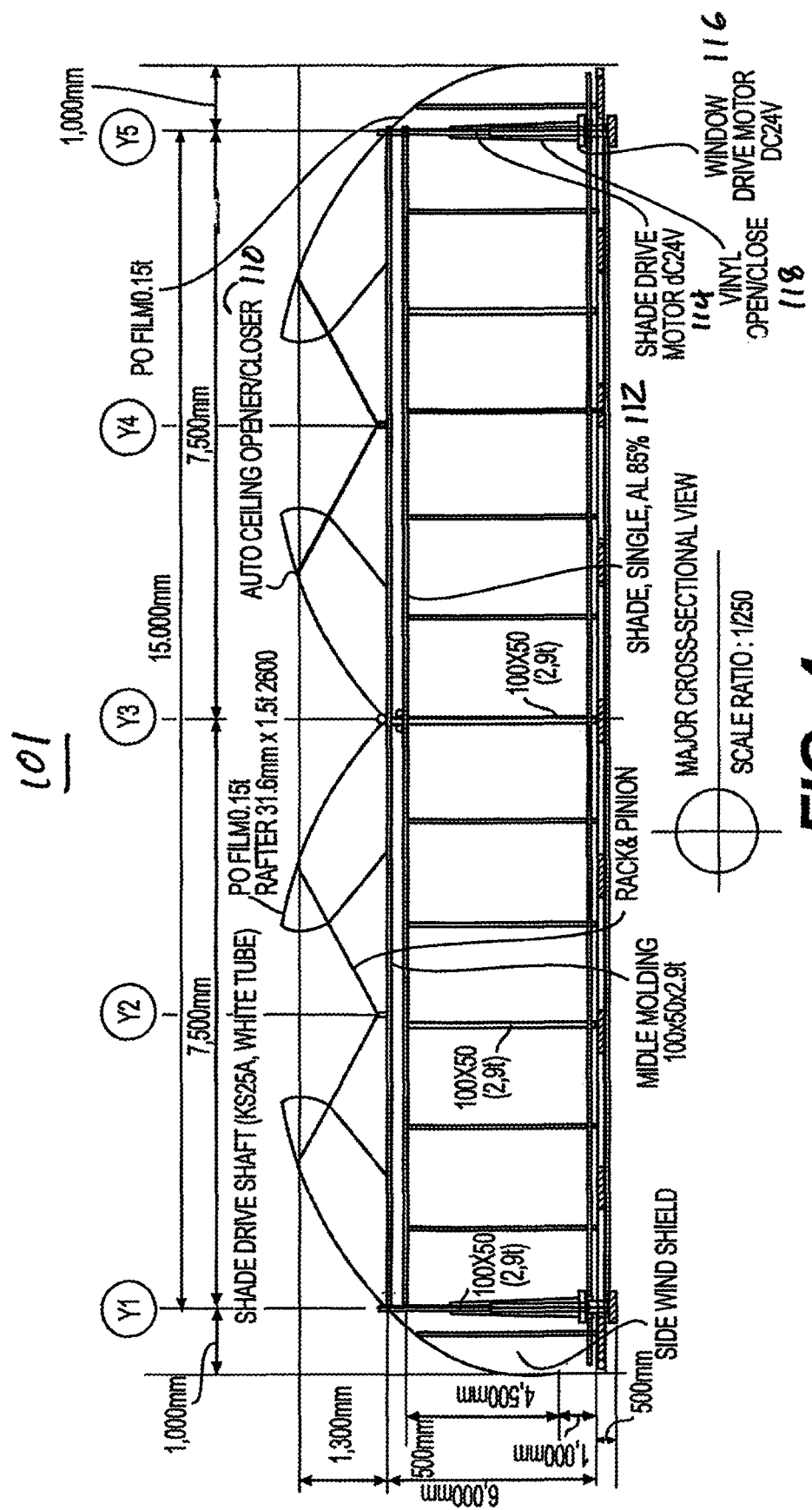

FOR MONITORING pH AND CONTROLLING CO2 SUPPLY
(FRESH WATER pH 7.26 OPTIMAL)

CULTURE MEDIUM STERILIZED FOR MICROALGAE HIGH DENSITY CULTURE, AND THE AIR COMPRESSION, AIR COOLING, CARBON DIOXIDE AUTOMATICALLY SUPPLIED, SEALED VERTICAL PHOTOBIOREACTOR, HARVESTING, DRYING APPARATUS AND CHARACTERIZED IN THAT TO PROVIDE A CARBON DIOXIDE BIOMASS CONVERSION FIXED, AIR AND WATER PURIFICATION METHOD USING THE SAME

FIELD OF THE INVENTION

The present invention relates to a device for the efficient culture and harvesting of microalgae, and a method for air purification and the biological treatment and purification of nitrogen and phosphorus in sewage, which is organic waste water, through fixation and conversion of carbon dioxide using biomass.

BACKGROUND OF THE INVENTION

Microalgae, which are photosynthesizing microorganisms, appeared on the primitive earth 2 to 3 billion years ago. Based on their powerful ability to prosper and propagate, they converted the carbons that were plentiful on the young Earth into organic materials through photosynthesis and discharged oxygen as the result of their metabolic ability. They made the appearance of animals possible, and survive to this day.

It cannot be denied that the current Earth environment is facing a grave crisis due to the depletion of energy sources and the impact of global warming owing to excessive emission of greenhouse gases. Accordingly, in order to reduce carbon dioxide emissions and the use of fossil fuels, bioenergy derived from organisms is gaining much attention as an alternative energy source. It can thus be said that it is strongly necessary for renewable, carbon-neutral biofuel to replace transport fuel, which is strongly dependent on conventional fossil fuels, in the near future.

Bioenergy is not only easier to store than other types of renewable energies, but can also be used directly in internal combustion engines. It can be mixed and used with normal diesel, and is a non-toxic, biodegradable substance. Until now, most biodiesel has been produced from palm oil, rapeseed oil, or other oil-rich plants. However, such plant-derived biodiesel is met with the problem of sustainability. For example, to produce the annual worldwide consumption of biodiesel (about 2 billion tons in 2015) from rapeseed would require about twice the land equal to the area of the Korean peninsula. Also, more than half of the total energy that can be produced is consumed during processing. These are the reasons why research and development into the production of biodiesel using microalgae has been gaining much attention recently.

The use of microalgae comes with many advantages. First, microalgae exhibit productivity characteristics far superior to plants in general. The fastest-growing microalgae divide and double in number every 3 hours. In addition to carbon dioxide, they can remove pollutants such as ammonia, nitrates, and phosphates, making them useful in waste water treatment as well. Also, cultured microalgae can, in addition to being an alternative to conventional fossil fuels, produce useful natural substances such as antioxidants. After extracting such substances, the byproducts can be used as feed or fertilizer, making them a fuel source that can be utilized for a wide variety of purposes.

However, there are various technical hurdles to be overcome for the mass culturing of microalgae. Processes for the culture of microalgae account for more than 50% of total costs, followed by harvesting, concentration, drying, and separation and extraction. Existing culture methods include registered Korean Patent No. 10-0679989 (Raceway-type outdoor mass microalgal culture vessel provided with seed culture vessel) and published Korean Patent No. 10-2012-0014387 (Photobioreactors for microalgal mass cultures and cultivation methods using them). However, the conventional raceway pond culture system and photobioreactors require a broad installation area and high initial installation costs. In the case of small raceway ponds, which have low initial facility costs, the forming of biofilm by the microalgae and the long culturing periods result in lower yields. In addition, coagulants, which are chemical agents, are used for harvesting, resulting in secondary water pollution problems. Photobioreactors, which have good yield rates, are limited in that they are restricted to a horizontal structure in order to induce a flow that prevents the attaching of algae to the walls. This horizontal structure not only makes difficult the introduction of carbon dioxide in the atmosphere, but also restricts the release of the photosynthetic product, oxygen. This oxygen poisoning limits growth productivity.

Ultimately, it can be said that, for the commercialization of microalgae, the development of a low-cost, high-energy combination technology that involves low initial facility costs and reduces operating costs by providing microalgal growth factors (light, carbon dioxide, nitrogen, phosphorus, trace minerals) at low cost is urgent.

SUMMARY OF THE INVENTION

The foregoing needs are met, to a great extent, by the present invention, wherein in one respect a photobioreactor and method of growing and harvesting microalgae are provided that in some embodiments overcomes the disadvantages described herein at least to some extent.

An embodiment of the present invention pertains to a microalgae culture broth producing system including a device for culture broth sterilization using a micro bubble generator, an air compression and pressure equalization device for the injection of carbon dioxide and oxygen from the atmosphere into the culture broth, and an air chilling device to maintain suitable culture broth temperature in response to a water temperature being higher than a predetermined maximum temperature. The system also includes an automatic carbon dioxide supply device to promote photosynthesis, a sealed vertical photobioreactor configured to contain a culture medium inoculated with a microalgae, the vertical photobioreactor being configured to allow light into the culture medium, block out pollutants and increase dissolved carbon dioxide and oxygen concentration, a high-efficiency harvesting device using hollow fiber membranes, and a hot air drying device using the waste heat generated by air compression.

Another embodiment of the present invention pertains to a method for air and water purification and fixation or conversion of carbon dioxide with biomass includes the method steps of supplying air and water to be purified to a microalgae culture broth producing system. The microalgae culture broth producing system includes a device for culture broth sterilization using a micro bubble generator, an air compression and pressure equalization device for the injection of carbon dioxide and oxygen from the atmosphere into the culture broth, and an air chilling device to maintain suitable culture broth temperature in response to a water temperature being higher than a predetermined maximum temperature. The system also includes an automatic carbon dioxide supply device to promote photosynthesis, a sealed vertical photobioreactor configured to contain a culture medium inoculated with a microalgae, the vertical photobioreactor being configured to allow light into the culture medium, block out pollutants and increase dissolved carbon dioxide and oxygen concentration, a high-efficiency harvesting device using hollow fiber membranes, and a hot air drying device using the waste heat generated by air compression.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 4 is a cross-sectional view of the greenhouse for microalgae culturing according to the present invention.

DETAILED DESCRIPTION

Figure 1:
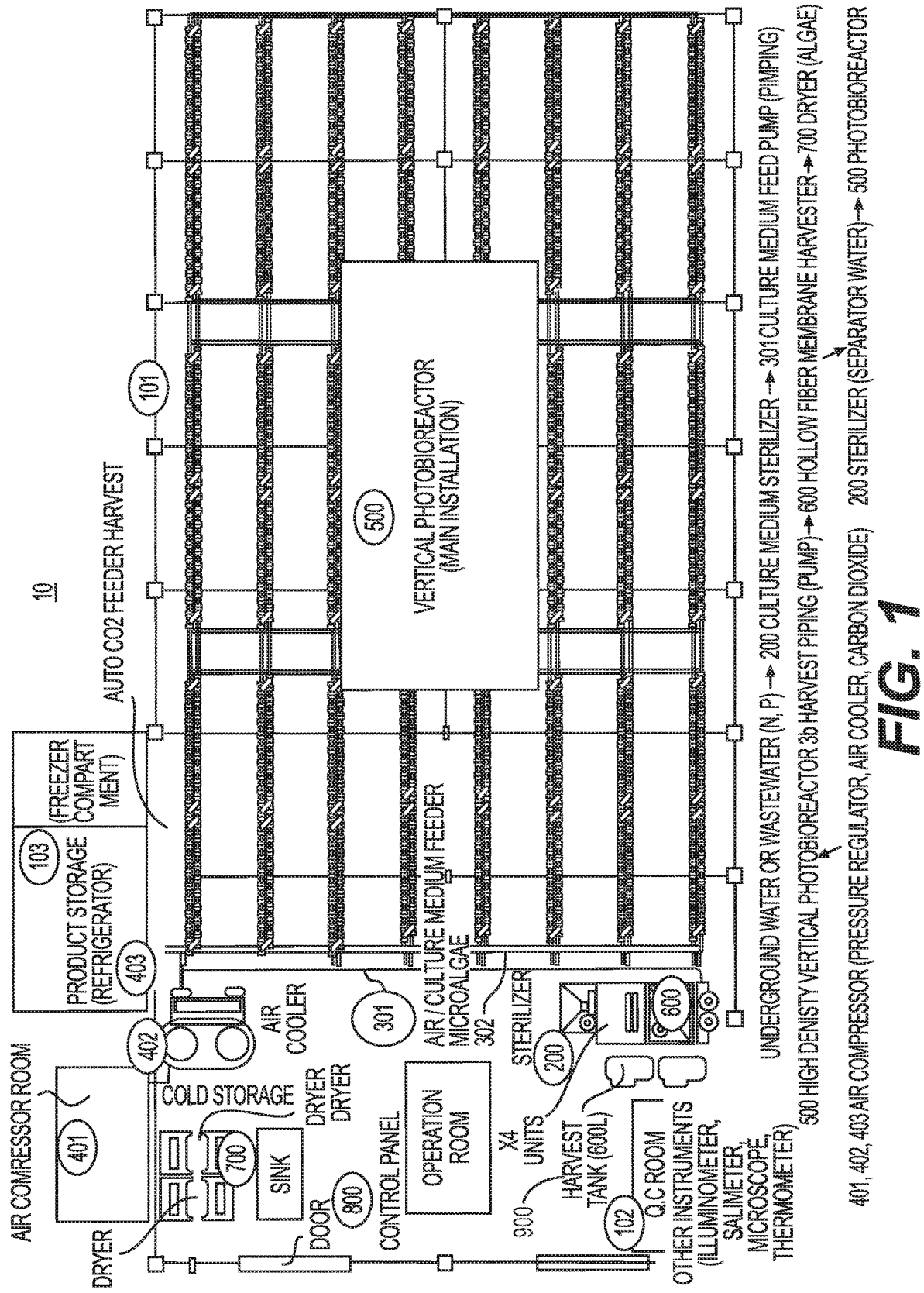
FIG. 1 is a perspective view of the facilities and equipment for efficient microalgae culturing according to the present invention.

Embodiments of the present invention relate to a microalgae culture broth producing system having a device for culture broth sterilization using a micro bubble generator, an air compression and pressure equalization device for the injection of carbon dioxide and oxygen in the atmosphere into the culture broth, and an air chilling device to maintain suitable culture broth temperature when water temperature is too high. The system also includes an automatic carbon dioxide supply device to promote photosynthesis, a sealed vertical photobioreactor to block out pollutants and increase dissolved carbon dioxide and oxygen concentration, a high-efficiency harvesting device using hollow fiber membranes, and a hot air drying device using the waste heat generated by air compression. Additional embodiments relate to a method for air and water purification and fixation or conversion of carbon dioxide using the microalgae culture broth producing system described herein.

According to embodiments of the present invention, nitrogen and phosphorus-rich waste water from sewage treatment plants can be sterilized using a micro bubble generator (sterilizer) and used in microalgae culture broth to culture microalgae which is passed through a hollow fiber membrane to harvest only the biomass (microalgae), after which the purified water is discharged into rivers or re-sterilized through the micro bubble generator and reused in culture broth to both save costs and improve the water environment.

The air pressurization and equalization device compresses carbon dioxide, oxygen, and nitrogen, etc. in the atmosphere and supplies these at a constant pressure into the photobioreactors, not only providing factors necessary for microalgae growth but also improving the air environment. The sealed vertical photobioreactor increases the infiltration rate of light, an element of photosynthesis, seals out competitor species or contaminants in the atmosphere, allows the easy dissolving of the foregoing growth factors of carbon dioxide, etc., and discharges oxygen, the metabolic product of photosynthesis, through a discharge pipe located on the top of the photobioreactor.

By using wastewater rich in nitrogen and phosphorus, and airborne pollutants such as carbon dioxide in the atmosphere as growth factors for microalgae, costs can be saved and the environment can be protected. In addition, the simple method of microalgae culturing and harvesting allows for daily harvesting at high concentrations and high purity.

Technical Problem: Until now, chlorine-based oxidizers (slightly acidic sodium hypochlorite, etc.) have been used for sterilization, which is the core step in the treatment of raw culture broth for microalgae culturing. However, such substances are not eco-friendly, and more economically feasible technologies which can do away with the production of harmful secondary byproducts such as trihalomethanes (THM) and halogenic acetic acid (HAA) need to be developed.

It is necessary to develop facilities that can maximize microalgae production through optimization of growth conditions, comprising a culturing device able to culture various types of microalgae throughout the year at low cost and high efficiency without contamination by indigenous microalgae, a device able to harvest this microalga effectively, and other equipment such as pressurized air generators and pipes for the supply and harvesting of culture broth which can support these devices.

In order to maximize productivity, BATCH TYPE (method in which inoculation is followed by batch harvesting when peak growth is reached) methods such as the conventional raceway pond culture system or photobioreactor should be avoided. The method should allow for continuous daily harvesting to maintain high growth density and the optimization of growth conditions such as lighting and nutrition.

Using such technologies, other technologies such as devices which purify air through the biomass conversion of carbon dioxide, and devices that purify waste water by biologically treating the large amounts of nitrogen and phosphorus contained within, can be developed.

Technical Solution: To achieve the abovementioned objectives, the present invention provides a vinyl greenhouse in which all culture-related equipment is contained, to allow for year-round culturing regardless of climate. As for the method for removal of indigenous microalgae or pathogens in waste water and the sterilization of the vertical photobioreactor, use of micro bubbles in the raw culture broth causes solids in the water to rise to the surface for effective removal, and the introduction of ozone, a strong oxidizer, into the raw water causes the dissolved ozone and bubbles in the water to spread and drift in the water until water pressure causes them to burst. The hydroxyl radicals ($OH^-$) that are produced when the ozone molecules are within the bubbles purify and completely sterilize the raw culture broth, replacing conventional chlorine-based oxidizers.

Carbon dioxide, nitrogen, and oxygen, which are key elements of photosynthesis, are compressed to 10 bar using an air compressor and passed through multiple stages of microfilters to filter out competing species or pathogens in the air. This purified compressed air is fed 24 hours a day through pipes into the bottom of each photobioreactor. During day hours with sunlight, the carbon dioxide that exists at a concentration of 350 ppm in the air is used for photosynthesis, and during night hours, when there is no light, the oxygen in the atmosphere that is required for respiration by the microalgae is supplied, providing optimal growth conditions. Also, a vertical photobioreactor is provided, meaning that the compressed air that is introduced through the lower pipes rises to the surface, forming bubbles, and causing natural ripples. This not only prevents the microalgae from attaching themselves to the wall surfaces, but also induces the dissolving of carbon dioxide and nitrogen, etc. in the atmosphere into the culture broth. Under these optimal growth conditions, rapid growth takes place. When the concentration reaches its peak, at which sunlight is blocked out, ½ is harvested at 24 hours to maintain a culture concentration optimal for light absorption. The photobioreactor is replenished with an amount of culture broth equal to the amount harvested, along with the nutrients necessary for growth.

Through the foregoing method, high-density culturing is possible year-round regardless of climate, even in limited space.

Effects of embodiments of the invention: The freely available carbon dioxide and nitrogen, etc., in the environment are used, improving the atmospheric environment, and the phosphorus and nitrogen in treated waste water can be used in the culture broth to achieve water purification effects.

By using pollutants as resources in the culture of microalgae, a positive circulation of resources can be induced, and economic feasibility can be secured by minimizing production costs.

While the lowering of productivity due to culture broth contamination has been the greatest hurdle to microalgae culturing until now, eco-friendly ozone and hydroxyl radical ($OH$—) sterilization overcome this obstacle, and a sealed structure for the photobioreactors protects the cultures from competing algae or pollutants in the air, providing optimal growth conditions.

The vertical structure facilitates harvesting and the supply of culture broth, allowing for harvesting at 24 hours and optimal light conditions to maximize productivity.

The harvested microalgae is passed through a hollow fiber membrane to separate the microalgae from the water. The water is then sterilized with a micro bubble generator/sterilizer, and reused in culture broth. The concentrated microalgae is dried out using the warm air discharged from the compressor.

A microalgae growth and harvesting system 10 according to embodiment of the present invention is shown in FIG. 1. As shown in FIG. 1, the microalgae growth and harvesting system 10 includes a greenhouse 101, a quality control room 102 and a freezer compartment 103. The microalgae growth and harvesting system 10 also includes a sterilizer 200 such as a micro bubble generator for generating a supply of pressurized ozone to sterilize incoming growth media.

The present invention relates to a method for continuous and economic mass production of microalgae-derived biomass without contamination.

Microalgae are primary producers that produce organic compounds through photosynthesis. Their product, biomass, is a substitute for the liquid energy of fossil fuels, while their pigment assimilation substances, with the powerful antioxidative abilities, are capable of producing useful eco-friendly natural substances such as drugs. Microalgae are emerging as an alternative to various petrochemical products, and, being a nutritionally complete food, are being used for food or health food supplements. After extracting these useful substances, the byproducts can be used as animal feed or fertilizer. Recently, organic microalgae byproducts are being used to promote plant growth and for pest prevention.

The success of plants that mass produce microalgae is determined by the handling of water (culture broth), the most important of the four elements (water, carbon dioxide, light, nutrients) required for the culture of microalgae.

Groundwater, lakes, rivers and seawater are the main sources for the water in microalgae culture broth. However, due to rapid industrialization in the 21st century, serious air, water and soil pollution have resulted. This means that raw water cannot be used as-is, but must be completely sterilized to remove any foreign debris, toxins, residual antibiotics and microbes, etc., in the water.

Until now, chlorine-based oxidizers (slightly acidic sodium hypochlorite, etc.) have been used for sterilization, which is the core step in the treatment of raw culture broth for microalgae culturing. However, such substances are not eco-friendly, and the production of harmful secondary byproducts such as trihalomethanes (THM) and halogenic acetic acid (HAA) have been a hurdle to the mass culturing of microalgae. Accordingly, the sterilizer 200 uses microbubbles in the raw culture broth to effectively remove solids in the water. The adding of ozone, a strong oxidizer, into the raw water causes the dissolved ozone and bubbles in the water to spread and drift in the water until water pressure causes them to burst. The hydroxyl radicals (OH—) that are produced when the ozone molecules within the bubbles purify and completely sterilize the raw culture broth.

The composition and performance of the micro bubble generator for the treatment of the microalgae culture broth are as follow: 1) Composition;—Pump: 5~10 tons/hour—Gases introduced: Air, oxygen, ozone; and 2) Performance;—bubble size: <20 micrometers—Dissolved gas concentration: >80%—Allowable size of solids: <5 mm.

The microalgae growth and harvesting system 10 includes a microalgae culture medium feeder apparatus 301, an air/$CO_2$ feeder apparatus 302, one or more compressors 401 that generates compressed air, a high pressure tank 402 to store the compressed air from the compressor 401, an air chiller 403 to cool compressed air and a vertical photobioreactor system 500. In a particular example, the photobioreactor system 500 includes one or an array of vertically arranged photobioreactors (V-PBR).

Selected and incubated microalgae, cultured up to 50 million cell/ml and up to 200 L volume, will be filled into one vertical photobioreactor (V-PBR) unit. One unit of vertical photobioreactor (V-PBR) comprises 20 tubes and total filled cultural water volume is about 2,000 L. Each tube size is Φ14 mm×4,000 mm and material made from polycarbonate or other transparent polymers. Each V-PBR unit can be operated independently or as a photobioreactor system 500.

In one embodiment, after filling between 170 L to 200 L of incubated microalgae as a seed into the V-PBR unit, then fill about 1,300 L to about 1,800 L of cultural water through the microalgae culture medium feeder apparatus 301 and air/$CO_2$ feeder apparatus 302. Before filling cultural water into the V-PBR unit, cultural water must be sterilized in a tank using sterilizer 200. In one embodiment, the sterilizer 200 is a micro bubble generator using oxygen and ozone gas as the bubble gas. The sterilizer 200 contains oxygen and ozone generator in a console box (see FIG. 8) and it generates oxygen by using air and the generated oxygen in turn generates ozone. The sterilized cultural water can be stored for about 24-48 hours in a tank before use in order to minimize dissolved oxygen and ozone level in cultural water.

The purified and sterilized culture broth is introduced into the vertically arranged photobioreactors 500 by being pumped through the connected microalgae culture medium feeder apparatus 301.

The vertical photobioreactors 500 are inoculated with the high-concentration microalgae cultured in the intermediate reactor (microalgae culture medium feeder apparatus 301) through pipes installed on the bottom of the vertical photobioreactors, after which an appropriate amount (0.5% of the raw culture broth) of nutrients is introduced.

The air compressed by the air compressor 401 is temporarily stored in a pressure regulating (high pressure tank) device 402 (up to 10 bar pressure). Using the micro filters (e.g., 1×5 micron, 1×1 micron, or 1×0.1 micron) in the air chiller 403, any file dust particles of indigenous microalgae (competing microalgae or pathogens, etc.) are filtered out at the set air pressure.

The purified air (including carbon dioxide, nitrogen and oxygen) is moved through the air/$CO_2$ feeder apparatus 302 and is purified a second time when passing through the filter of the fine control device installed on the bottom of the vertical photobioreactors 500.

The air that is introduced forms air bubbles, rising to the top and creating ripples. This keeps the microalgae from attaching to the walls of the vertical photobioreactors 500 while growing, and blocking out sunlight. In addition, the culture broth moves horizontally and vertically, increasing opportunities for contact with light (growth factors) and promoting growth.

Some of the benefits of the air supply include supplying carbon dioxide, oxygen, preventing biofilm formation on the surface of the tube, even dispersion of microalgae, and controlling the cultural water temperature. It should be noted that there is about 0.03% (which is too high) of carbon dioxide in the air and by supplying air into the V-PBR's tube, the carbon dioxide can be diluted in the water and help microalgae's photosynthesis activity in daylight. In another embodiment, the carbon dioxide can be in liquid form. At night, microalgae need oxygen for their respiration. By supplying air at night, about 23% of oxygen in the air can be diluted in the water and helps the respiration by the microalgae. As the air is introduced, the air bubbles are traveling to the right, left and vertically up to the top of the V-PBR. These movements can help to mix the microalgae evenly in the water and increase their light contact ratio. In microalgae cultural environment, the water temperature is the most sensitive factor. By inserting air temperature control, cool and warm, water temperatures can be controlled more precisely.

Microalgae needs food for growing. As their food, inorganic nutrients such as nitrogen, phosphorus and minerals can be supplied and its total volume is about 0.2% to about 0.5% of total cultural volume. It can be supplied to V-PBR unit individually through the air/$CO_2$ feeder apparatus 302 or through mixing with microalgae culture medium feeder apparatus 301.

Once the peak (Ser. No. 10/000,000-50,000,000 cells/ml) is reached, ½ of the culture broth is recovered (harvested) at 24 hour intervals through the microalgae culture medium feeder apparatus 301 and/or the air/$CO_2$ feeder apparatus 302. This allows for the optimum culture competition for absorption of light for photosynthesis to be maintained. Before harvesting, cell number and size can be monitored and cell shape and status can be analyzed though equipment such as illuminator, salimeter, and the like. Harvested cultured water can be sent to 0.1 micron size of the hollow fiber membrane harvester 600 and it will be separated and delivered to two different harvest tanks 900. One tank 900 is for filtered cultured water without microalgae biomass and the other tank 900 is for cultured water with microalgae biomass. The vertical photobioreactor is replenished with an amount of ozone-sterilized culture broth equal to the amount harvested, adding the nutrients that are necessary for growth. In other words, refill the V-PBR with about 25% of harvested and separated cultured water and about 25% of normal water, which was sterilized using sterilizer 200 at least 24 hours ago. Once all tubes of the V-PBR are refilled, supply microalgae food (nitrogen, phosphorus and minerals) and air as the initial microalgae inoculation process.

The present invention, as described in the embodiments, allows for maximum productivity by repeating this culturing method. The culture broth recovered through the microalgae culture medium feeder apparatus 301 (high-density microalgae) is passed through a hollow fiber membrane separator 600 that employs the reverse osmosis principle to harvest the water and microalgae separately. The water is then purified and sterilized through the micro bubble generator 200 and reused in the photobioreactors 500. The harvested high-density microalgae is dried in a dryer 700 that uses the heat that is generated during air compression.

A control panel 800 is utilized to oversee the operation of the microalgae growth and harvesting system 10. The control panel 800 is configured to control the cultural water temperature through the air bubble air temperature generated by air chiller 403. The control panel 800 can also control the pH level of the cultural water in the tubes through the use of the carbon dioxide supply. Further, the control panel 800 can control and monitor the air bubble status (size, speed through water, etc.) through the air supply valve on the air compressor 401.

Figure 2:
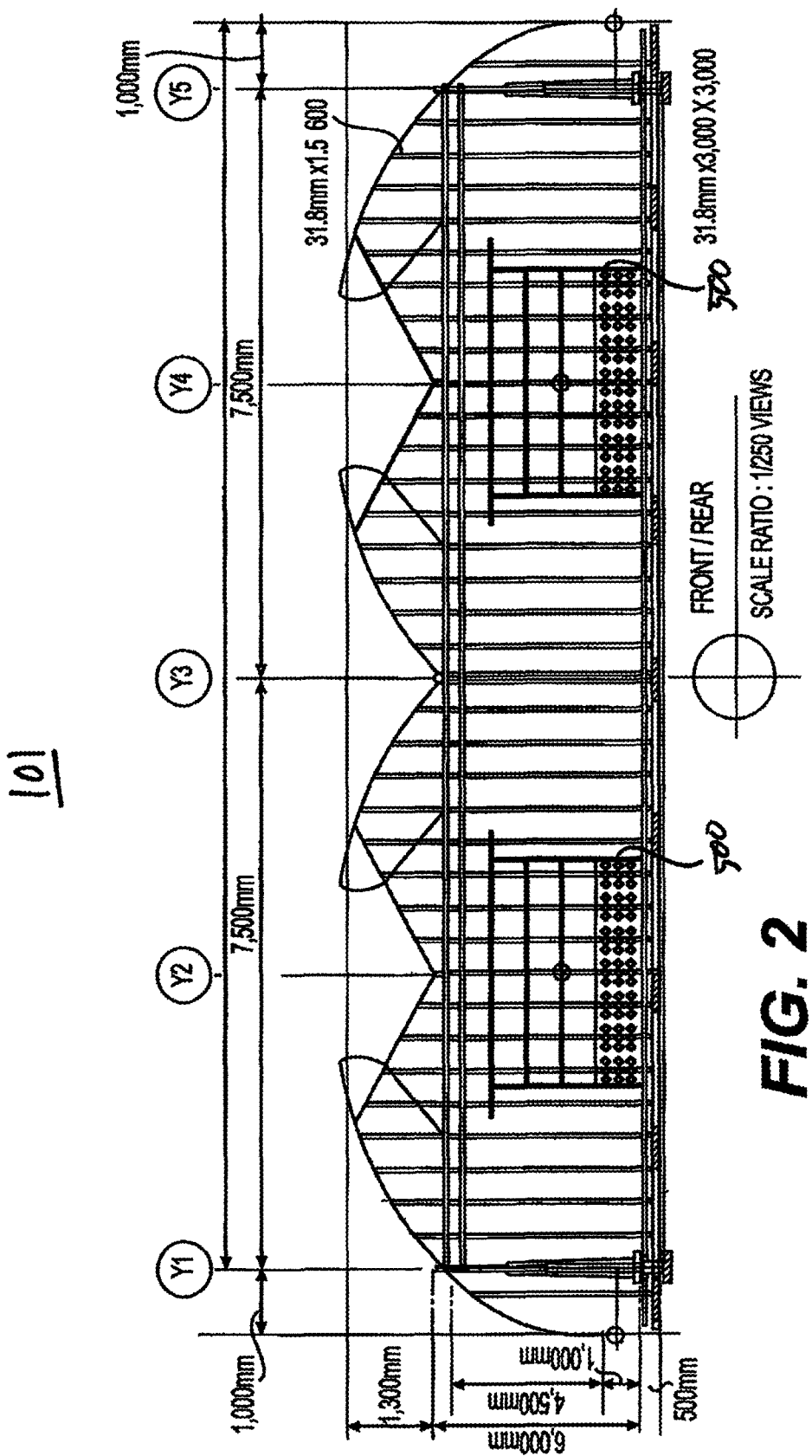
FIG. 2 shows front and rear views of the greenhouse for microalgae culturing according to the present invention.
Figure 3A:
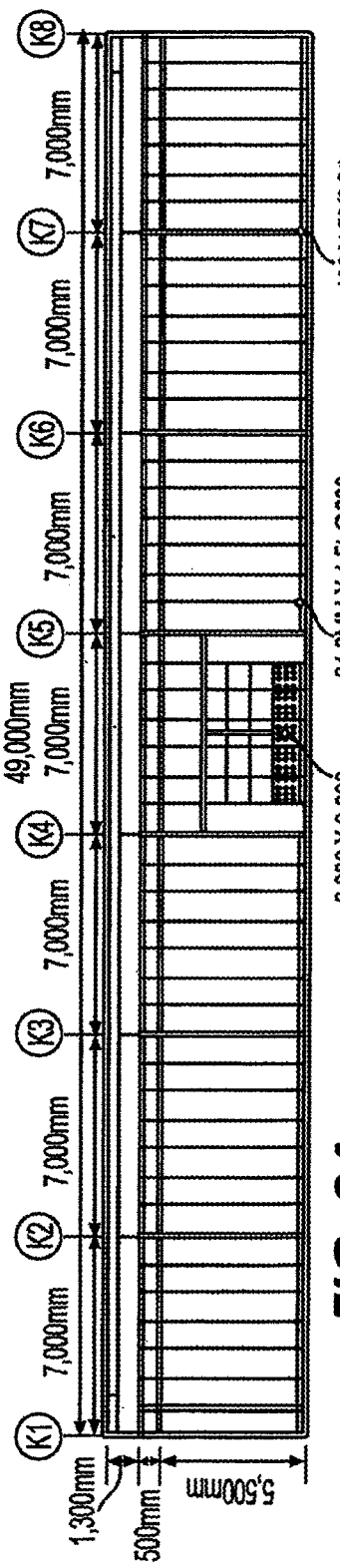
FIGS. 3A and 3B are left and right sides views of the greenhouse for microalgae culturing according to the present invention.
Figure 3B:
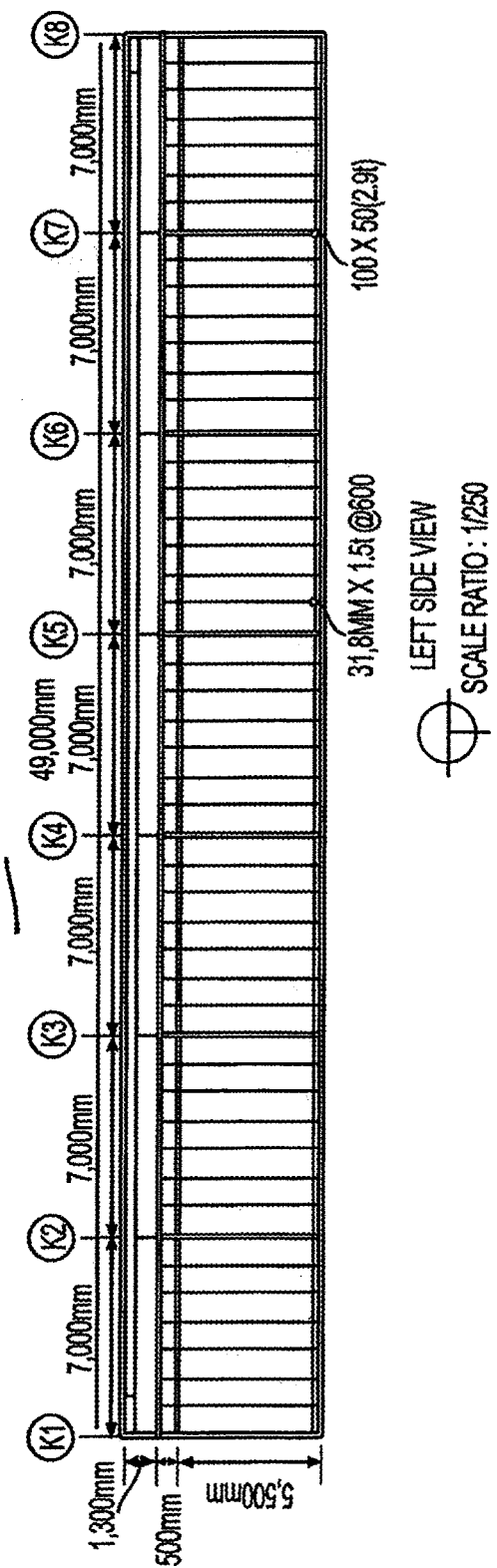

FIG. 2 shows front and rear views of the greenhouse 101 for microalgae culturing according to the present invention and FIGS. 3A and 3B are left and right side views of the greenhouse 101 for microalgae culturing according to the present invention. FIG. 4 is a cross-sectional view of the greenhouse 101 for microalgae culturing according to the present invention showing an auto ceiling opener/closer 110, a shade 112, a shade drive motor 114, a window drive motor 116, and window 118 operated by the window drive motor 116.

Figure 5:
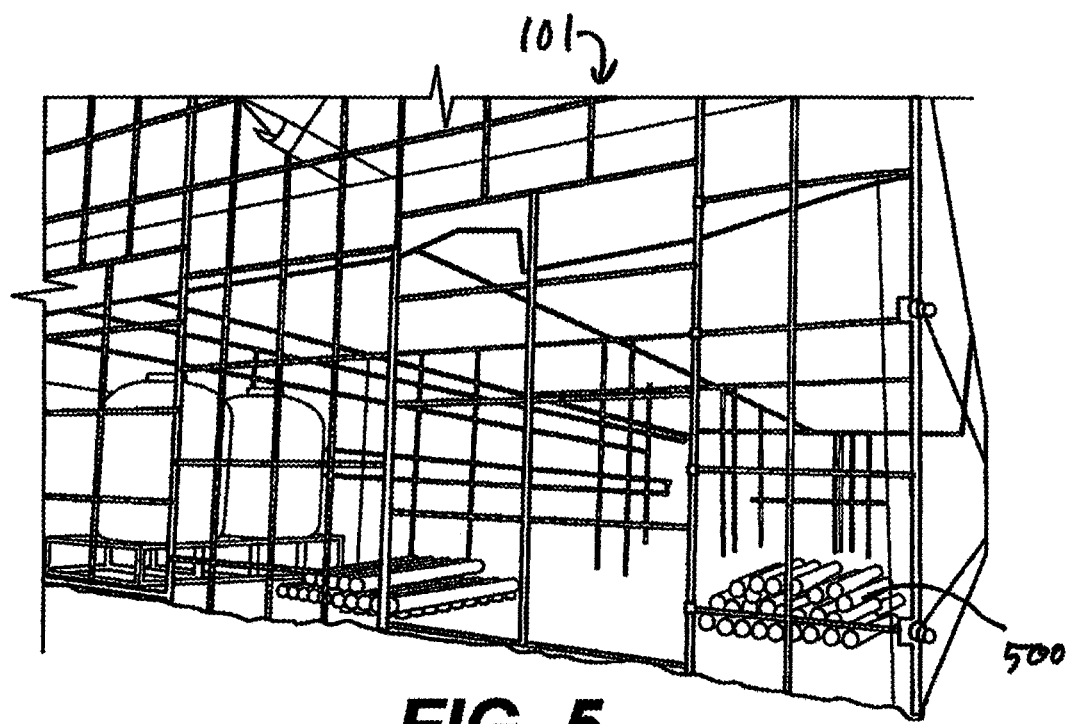
FIG. 5 is a first perspective view of the greenhouse installed for microalgae culturing according to the present invention.
Figure 6:
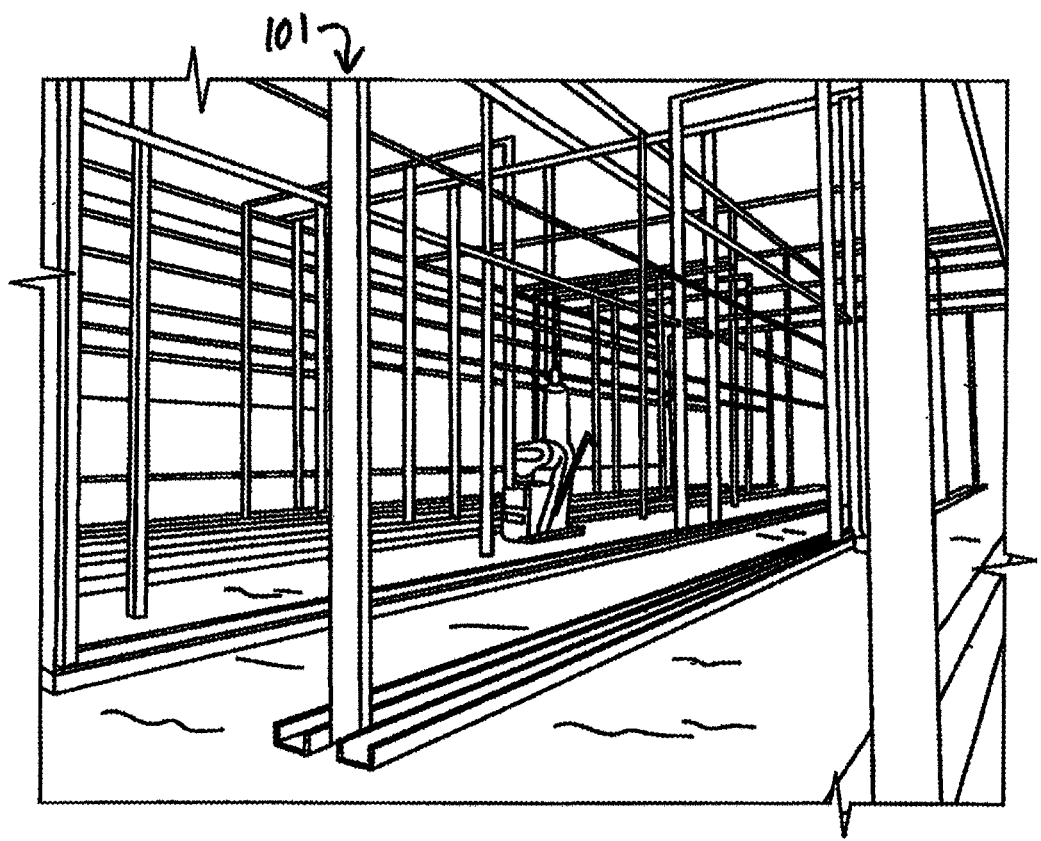
FIG. 6 is a second perspective view of the greenhouse installed for microalgae culturing according to the present invention.
Figure 7:
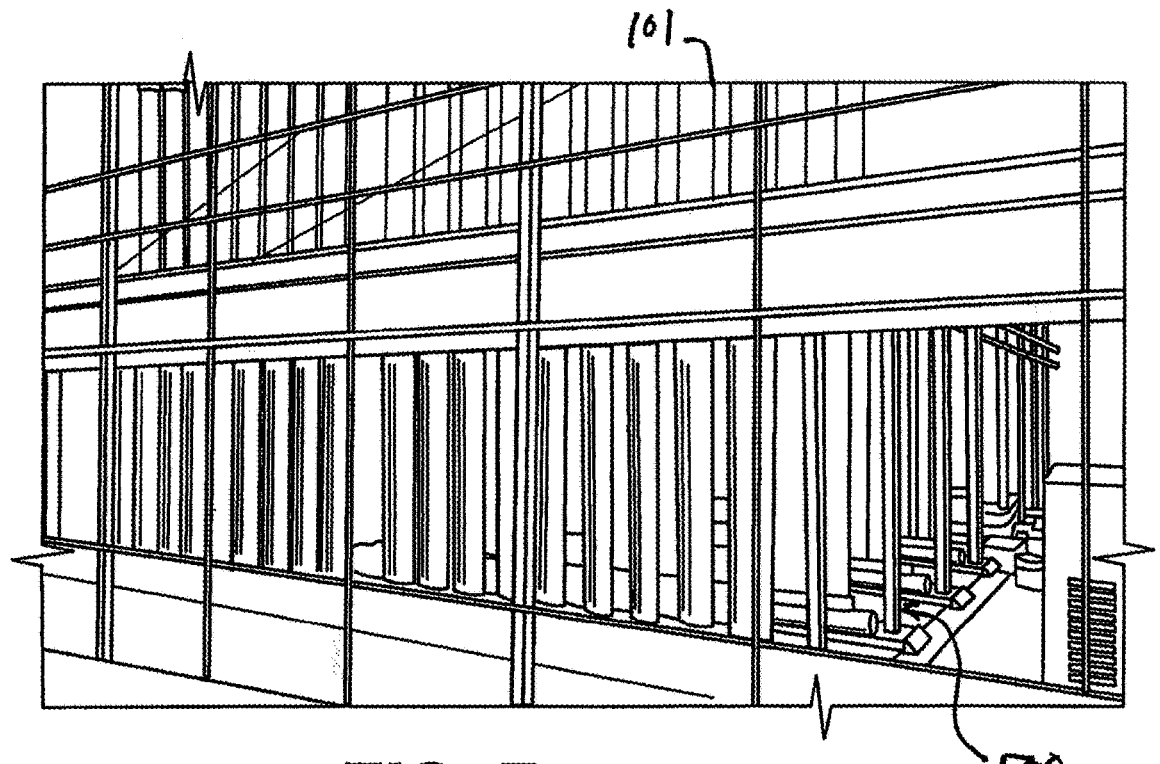
FIG. 7 is a third perspective view of the greenhouse installed for microalgae culturing according to the present invention.

FIG. 5 is a first perspective view of the greenhouse 101 installed for microalgae culturing according to the present invention showing the vertical photobioreactors 500 in a disassembled state. FIG. 6 is a second perspective view of the greenhouse 101 installed for microalgae culturing according to the present invention showing the area in which the photobioreactor 500 is to be assembled. FIG. 7 is a third perspective view of the greenhouse 101 installed for microalgae culturing according to the present invention showing the assembled photobioreactor 500 installed in the greenhouse 101.

Figure 8:
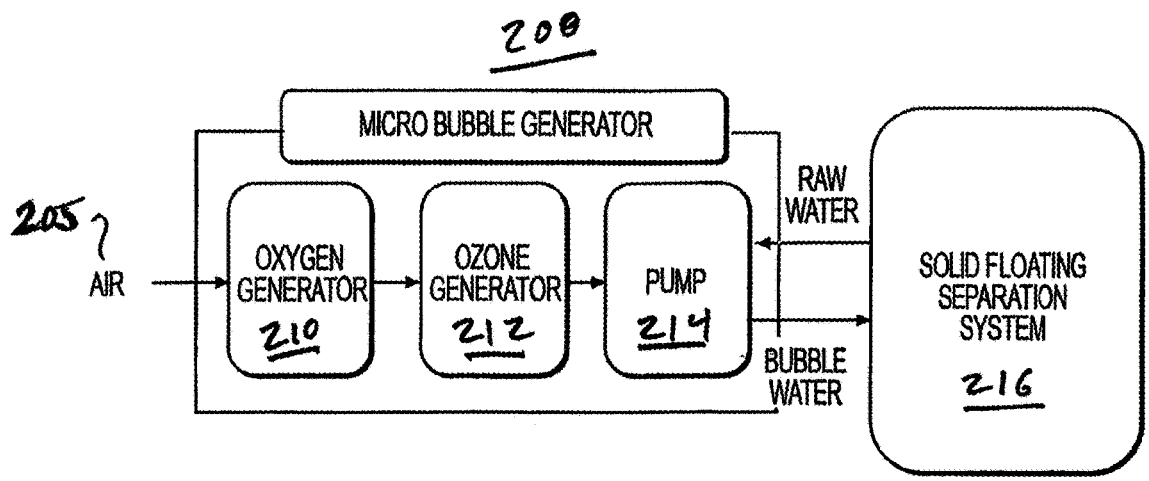
FIG. 8 is a structural diagram of the micro bubble generating device for sterilization of culture broth according to the present invention.

FIG. 8 is a structural diagram of the micro bubble generating device 200 for sterilization of culture broth according to the present invention showing the sterilizer 200 includes an oxygen generator 210, an ozone generator 212, a pump 214 and a float tank 216. Air 205 from the environment is taken into the micro bubble generating device 200. Culture broth in the form of raw water or sewage is placed in the float tank 216 and ozone is bubbled through the culture broth from below. Excess ozone is collected from the top of the float tank 216 and fed back to the bottom of the float tank 216.

Figure 9:
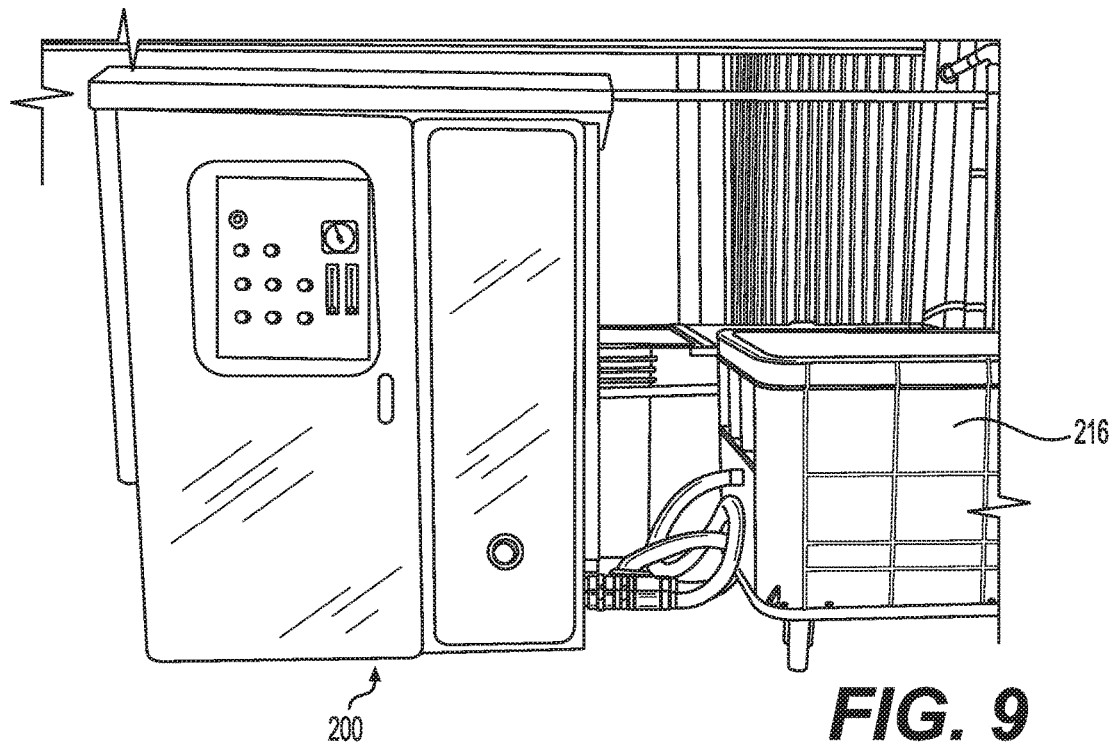
FIG. 9 is an illustration of the micro bubble generating device installed for sterilization of culture broth according to the present invention.

FIG. 9 is an illustration of the micro bubble generating device 200 installed for sterilization of culture broth according to the present invention showing the connection to the float tank 216.

Figure 10:
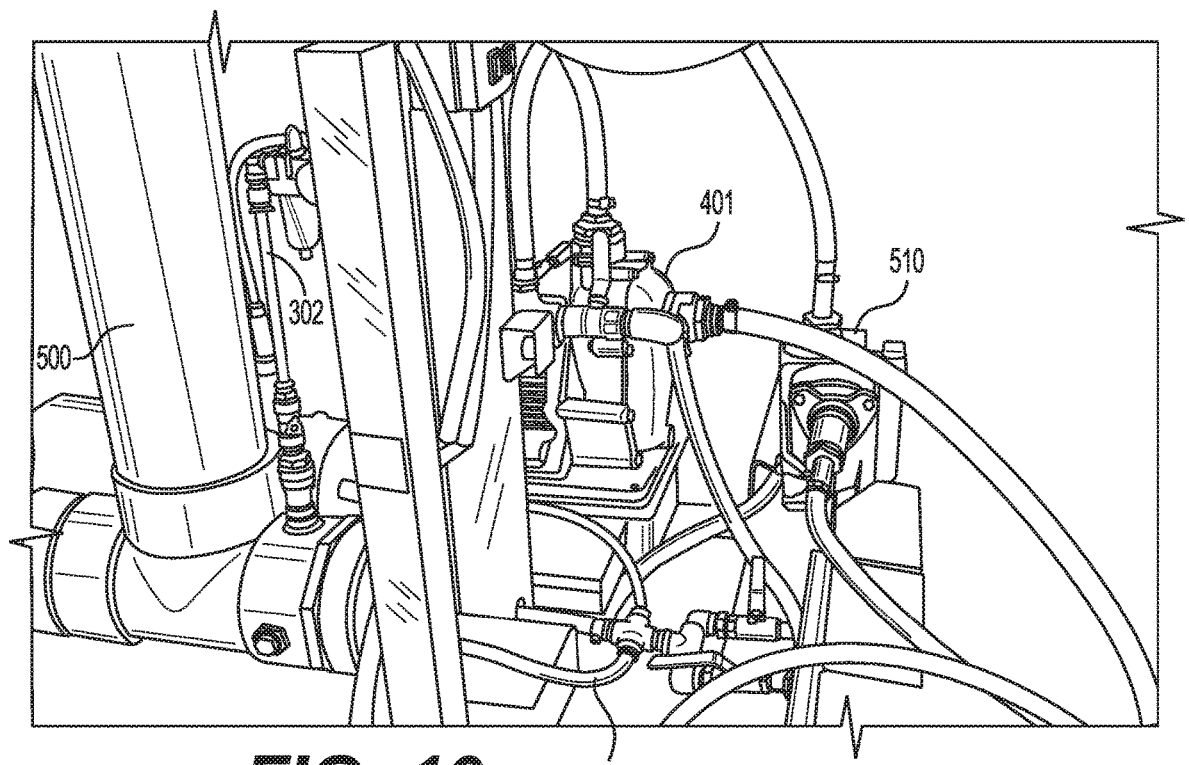
FIG. 10 is a first illustration of the culture broth and air (carbon dioxide and nitrogen) supply pipes according to the present invention.
Figure 11:
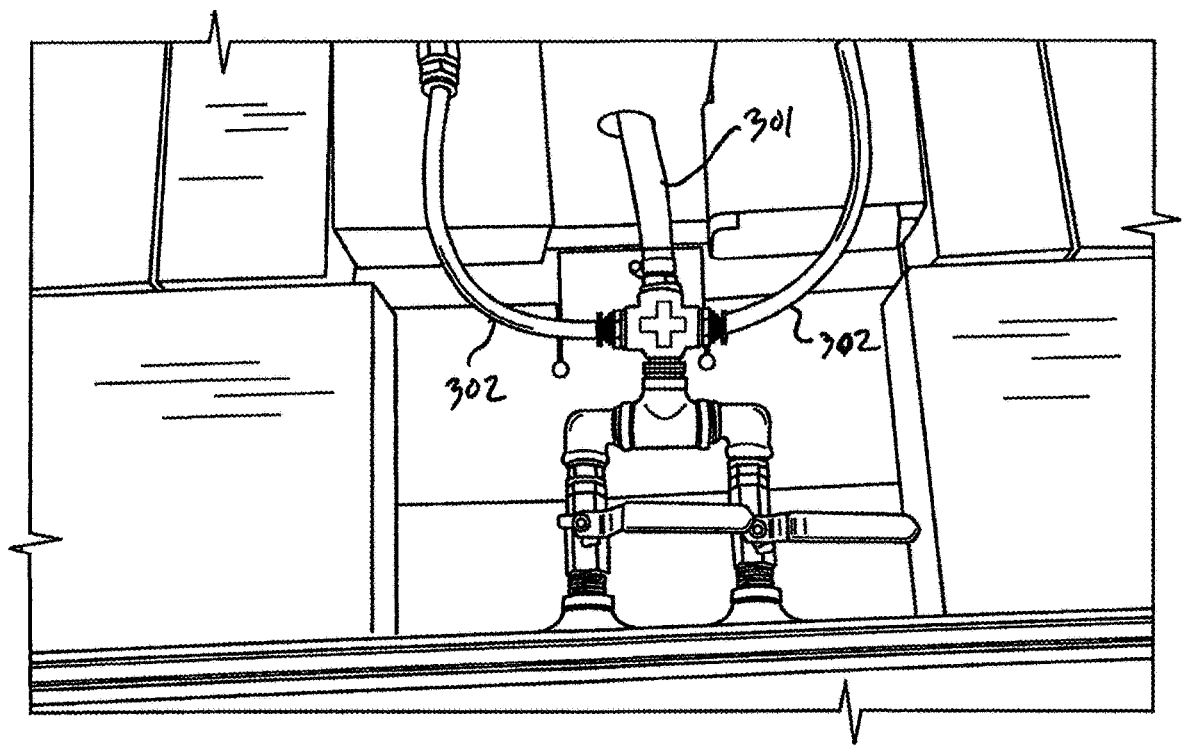
FIG. 11 is a second illustration of the culture broth and air (carbon dioxide and nitrogen) supply pipes according to the present invention.

FIG. 10 is a first illustration of the culture broth and air (carbon dioxide and nitrogen) supply pipes according to the present invention. As shown in FIG. 10, the photobioreactor 500 is supplied with air/$CO_2$ from the compressor 401 via the line of the air/$CO_2$ feeder apparatus 302 and the photobioreactor 500 is supplied with culture media from a pump 510 via the line of the microalgae culture medium feeder apparatus 301. FIG. 11 is a second illustration of the culture broth and air (carbon dioxide and nitrogen) supply pipes of the microalgae culture medium feeder apparatus 301 and of the air/$CO_2$ feeder apparatus 302 according to the present invention.

Figure 12:
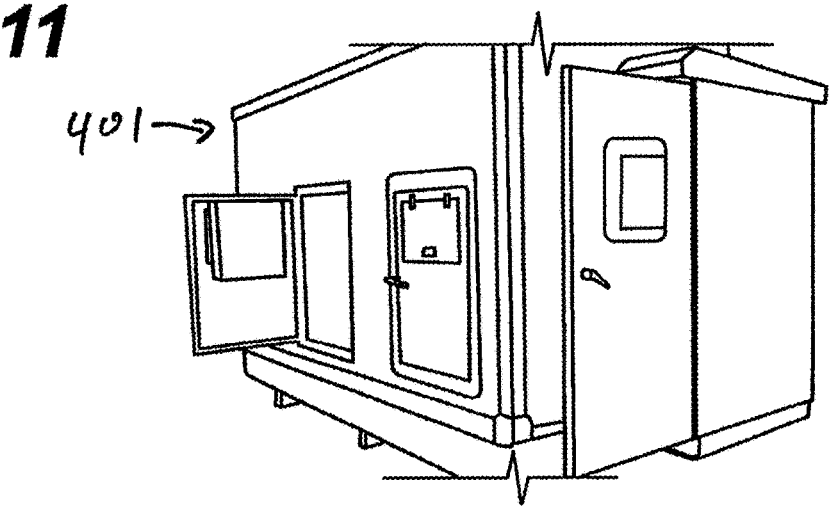
FIG. 12 is a first illustration of the air compressor installed according to the present invention.
Figure 13:
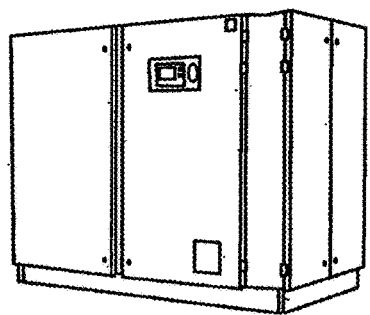
FIG. 13 is a second illustration of the air compressor installed according to the present invention.

FIG. 12 is a first illustration of the air compressor 401 installed according to the present invention and FIG. 13 is a second illustration of the air compressor 401 installed according to the present invention.

Figure 14:
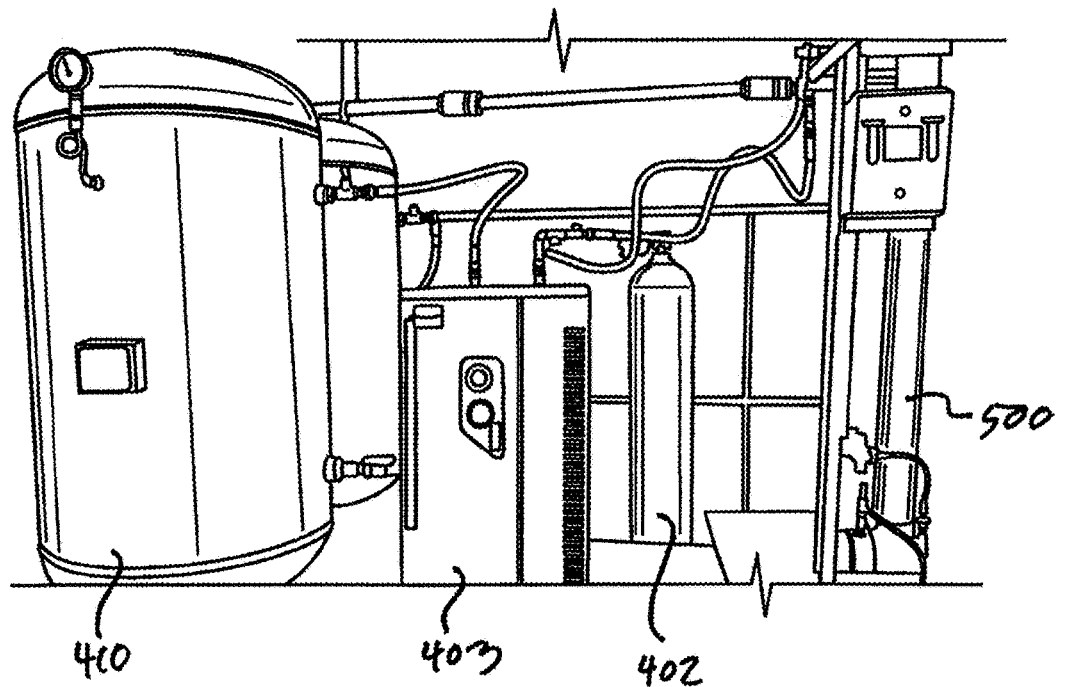
FIG. 14 is an illustration of the tank and air chilling device for compressed air pressure regulation installed according to the present invention.
Figure 15A:
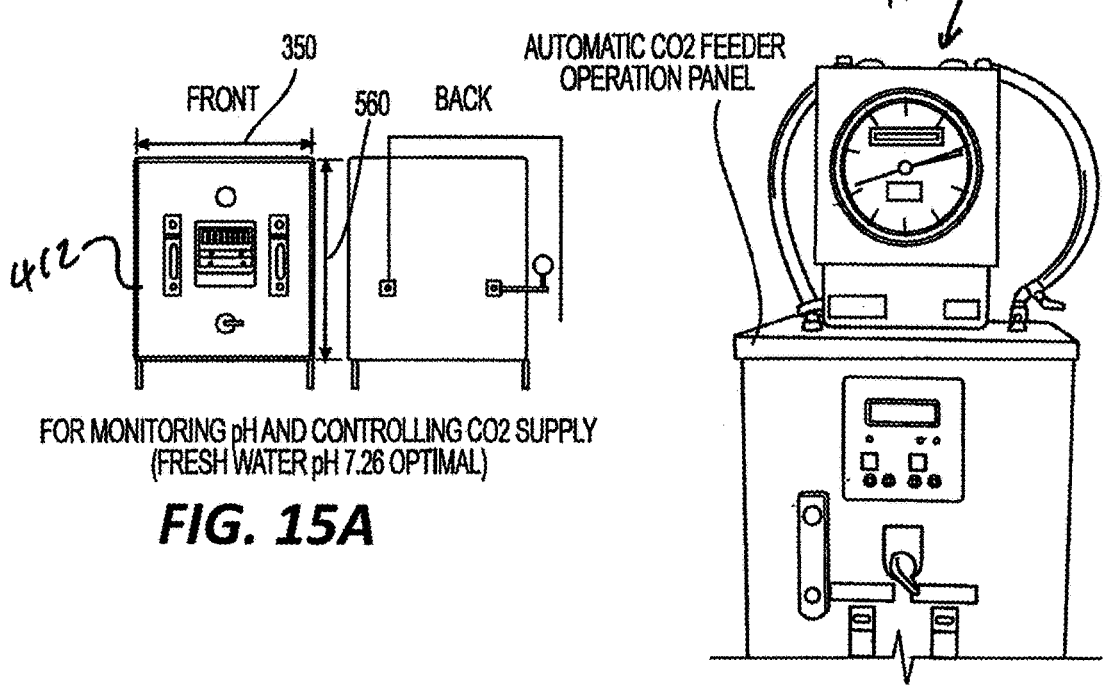
FIG. 15A is an illustration of the automatic carbon dioxide supply device installed and FIG. 15B is an illustration of a control panel of the automatic carbon dioxide supply device according to the present invention.
Figure 15B:
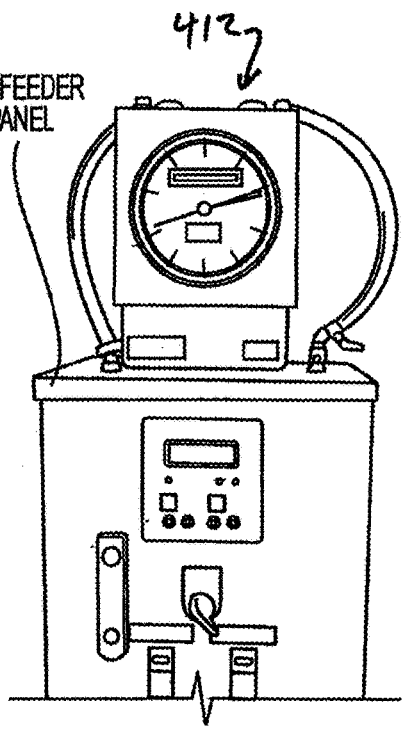

FIG. 14 is an illustration of the high pressure tank 402 and air chilling device, air chiller 403 for compressed air pressure regulation installed according to the present invention. Also shown in FIG. 14 is a storage tank 410 for culture media. FIG. 15A is an illustration of the automatic carbon dioxide supply device 412 installed according to the present invention, and FIG. 15B is an illustration of a control panel of the automatic carbon dioxide supply device 412.

Figure 16:
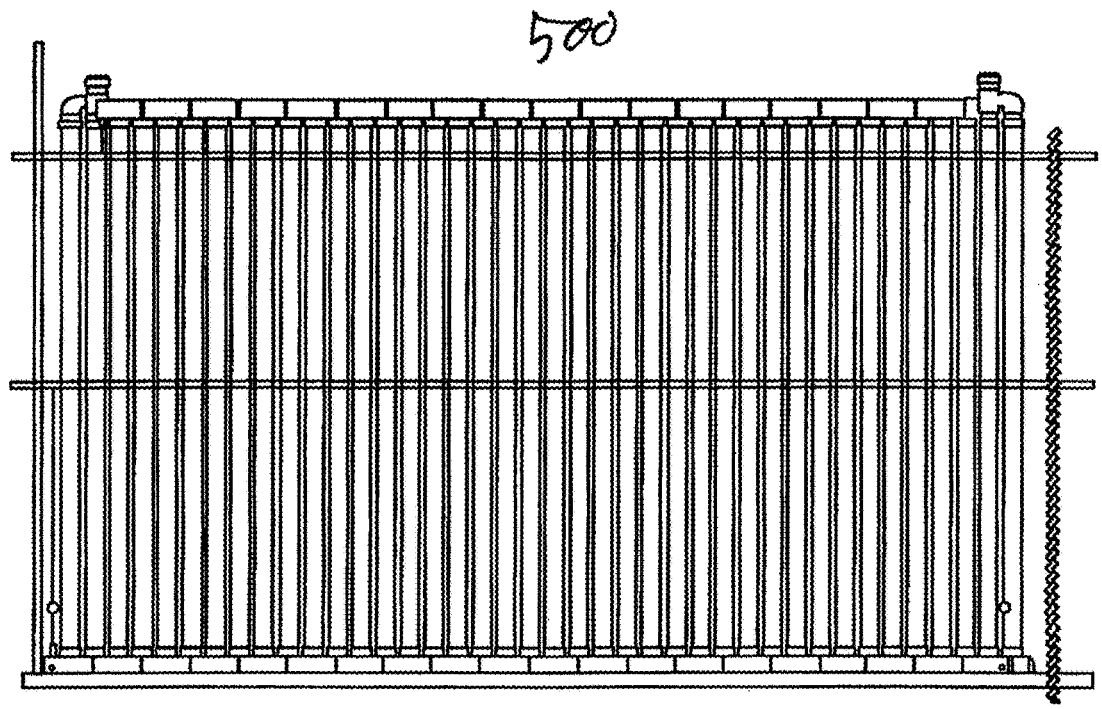
FIG. 16 is a side view of the vertical photobioreactor according to the present invention.
Figure 17:
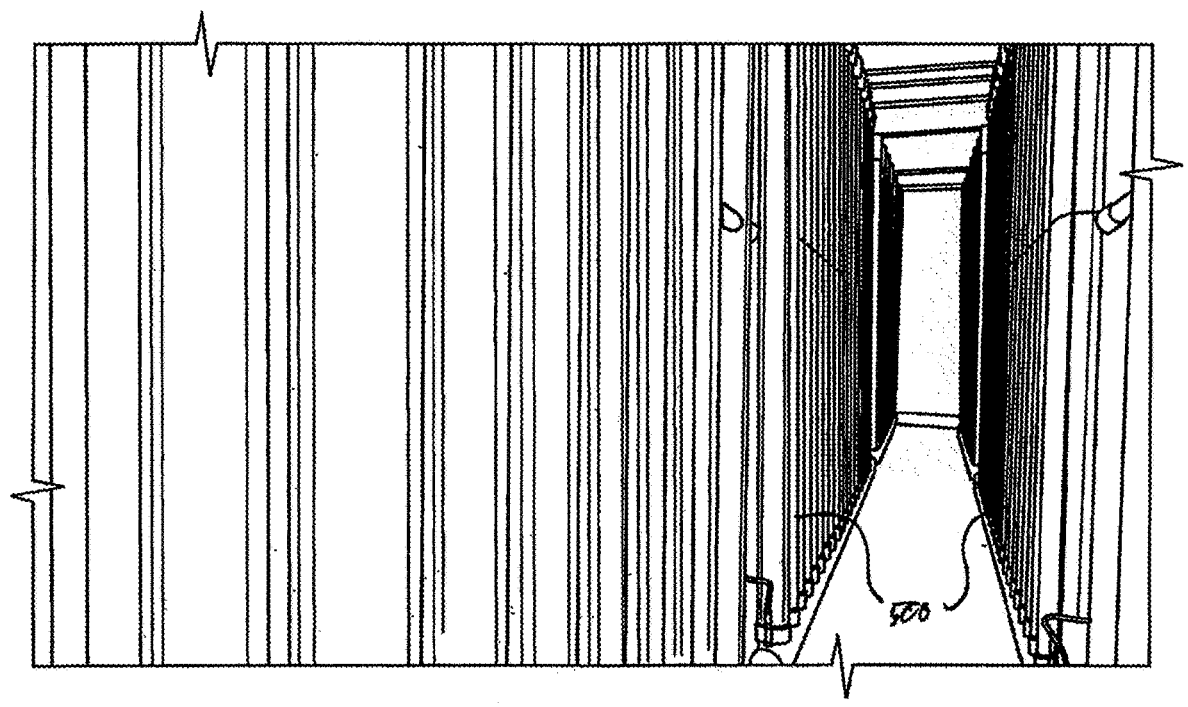
FIG. 17 is a perspective view of the vertical photobioreactor installed according to the present invention.
Figure 18:
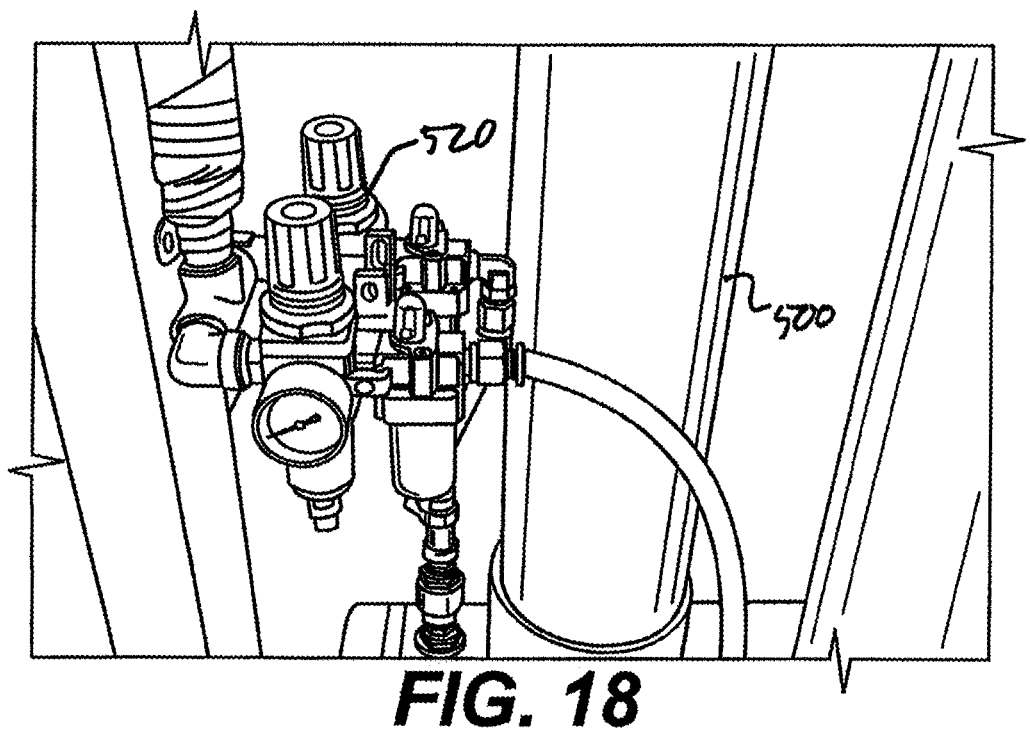
FIG. 18 is an illustration of the air pressure regulating device installed on the vertical photobioreactor according to the present invention.
Figure 19:
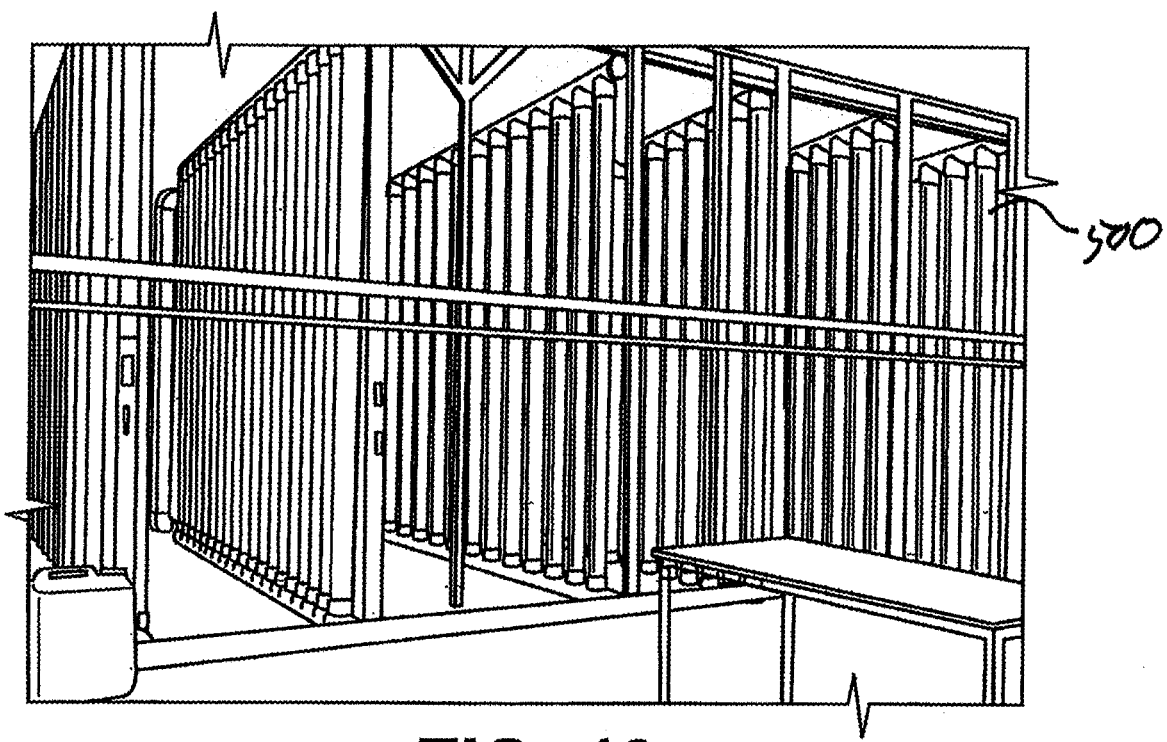
FIG. 19 is a second perspective view of the vertical photobioreactor installed according to the present invention.
Figure 20:
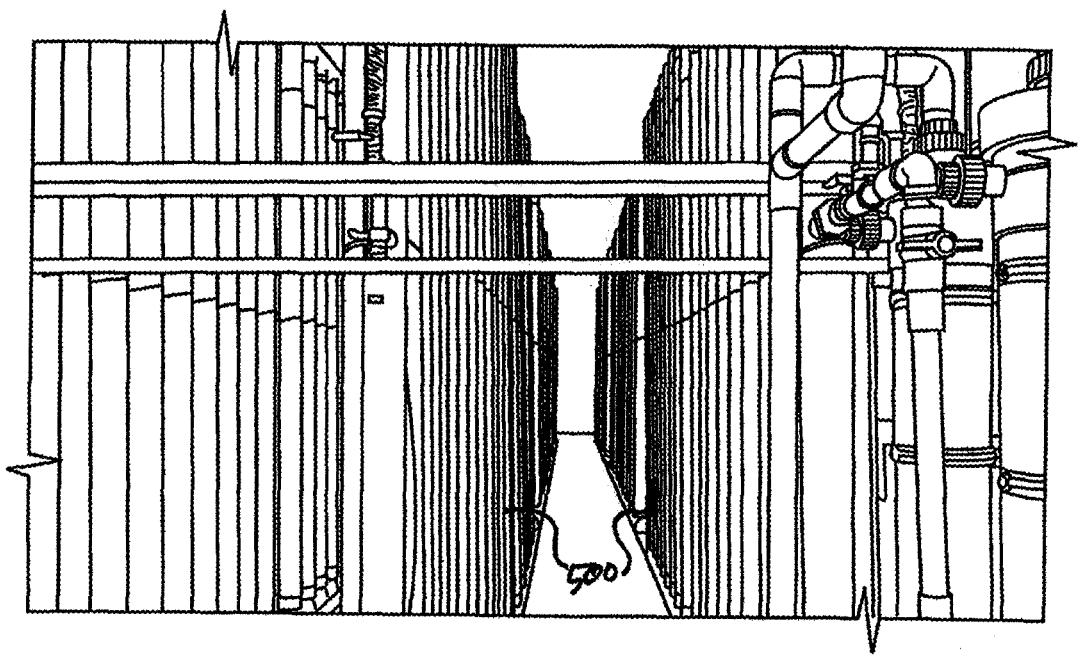
FIG. 20 is a third perspective view of the vertical photobioreactor installed according to the present invention.
Figure 21:
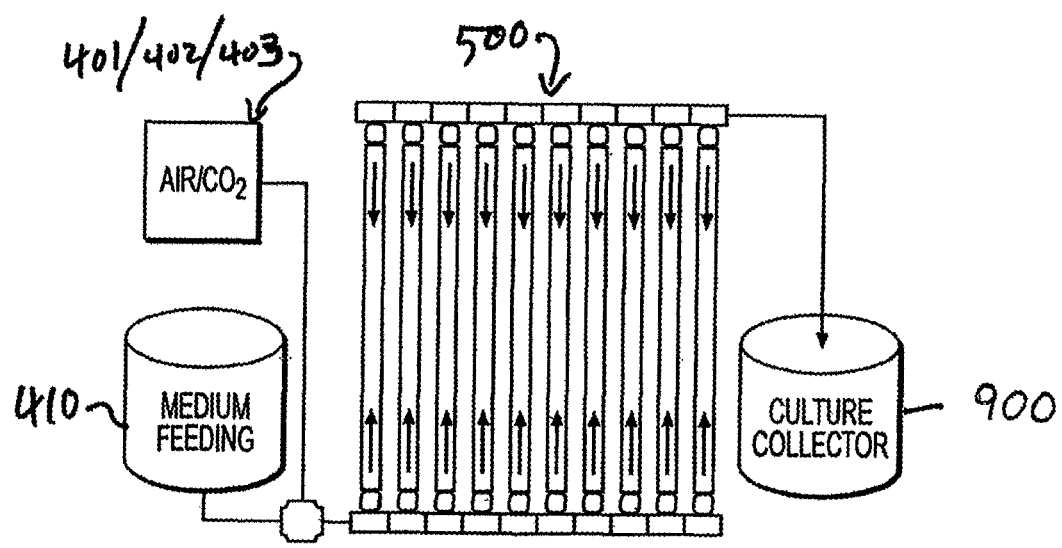
FIG. 21 is a block diagram of the vertical photobioreactor according to the present invention.

FIG. 16 is a side view of the vertical photobioreactor 500 according to the present invention and FIG. 17 is a perspective view of the vertical photobioreactor 500 installed according to the present invention. FIG. 18 is an illustration of an air pressure regulating device 520 installed on the vertical photobioreactor 500 according to the present invention and FIG. 19 is a second perspective view of the vertical photobioreactor 500 installed according to the present invention. FIG. 20 is a third perspective view of the vertical photobioreactor 500 installed according to the present invention. FIG. 21 is a block diagram of the vertical photobioreactor 500 according to the present invention. As shown in FIG. 21, air/CO2 is supplied via the compressor 401, tank 402, and air chiller 403. Media is supplied via the tank 410. The microalgae is grown in the vertical photobioreactor 500 and collected in a harvest tank 900.

Figure 22:
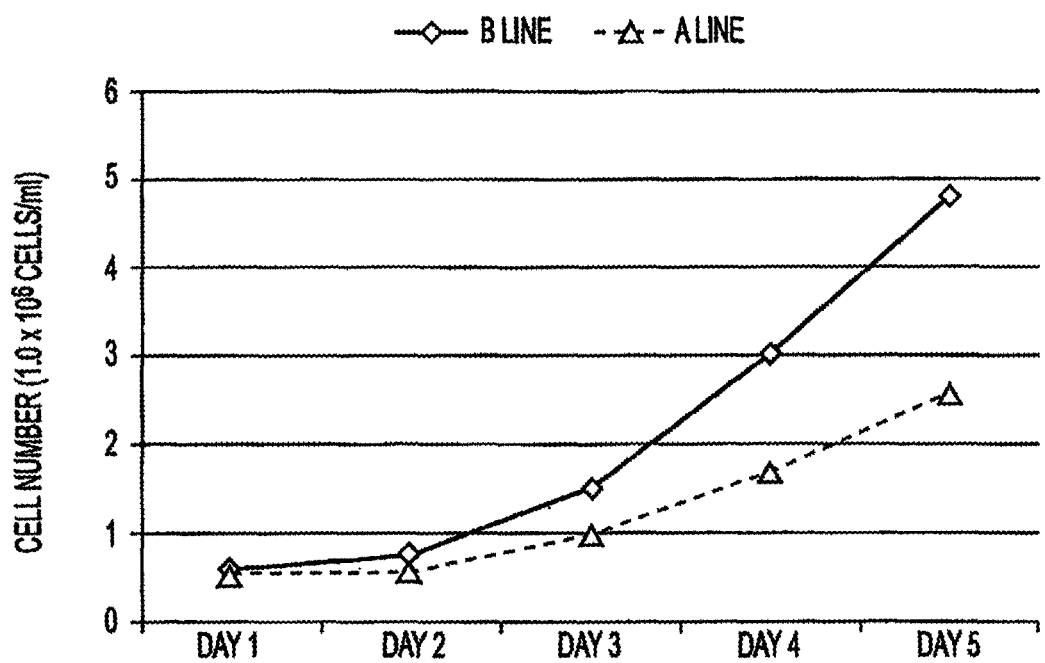
FIG. 22 is a daily growth graph for the vertical photobioreactor according to the present invention.
Figure 23:
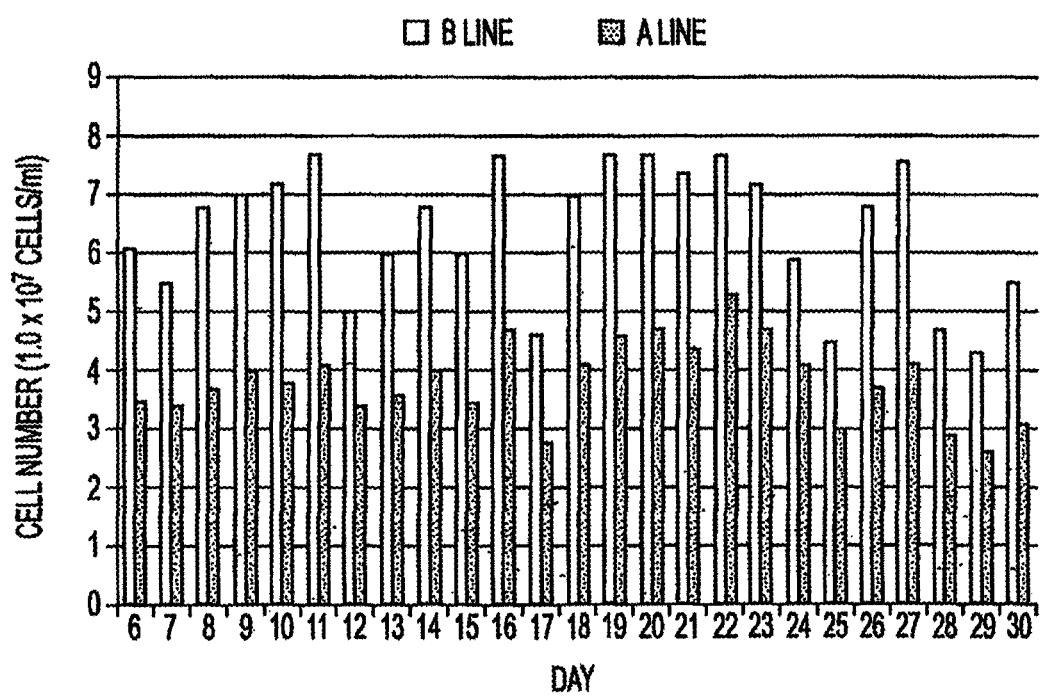
FIG. 23 is a monthly growth graph for the vertical photobioreactor according to the present invention.

FIG. 22 is a daily growth graph for the vertical photobioreactor according to the present invention and FIG. 23 is a monthly growth graph for the vertical photobioreactor according to the present invention.

Figure 24:
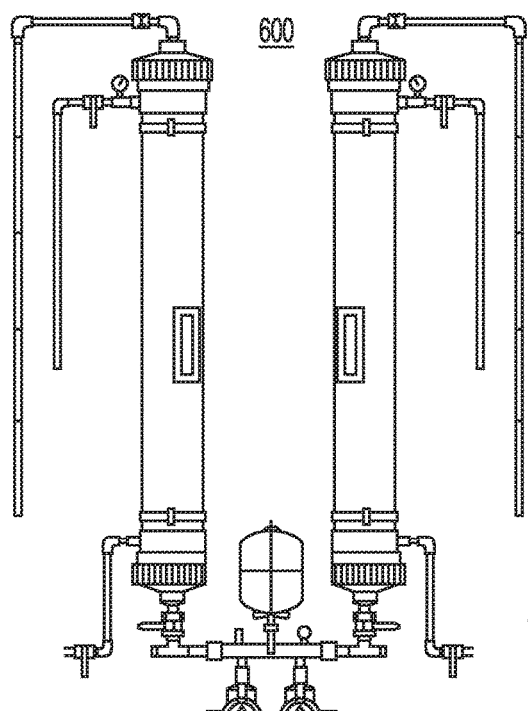
FIG. 24 is a front view of the hollow fiber membrane microalgae harvesting device according to the present invention.
Figure 25:
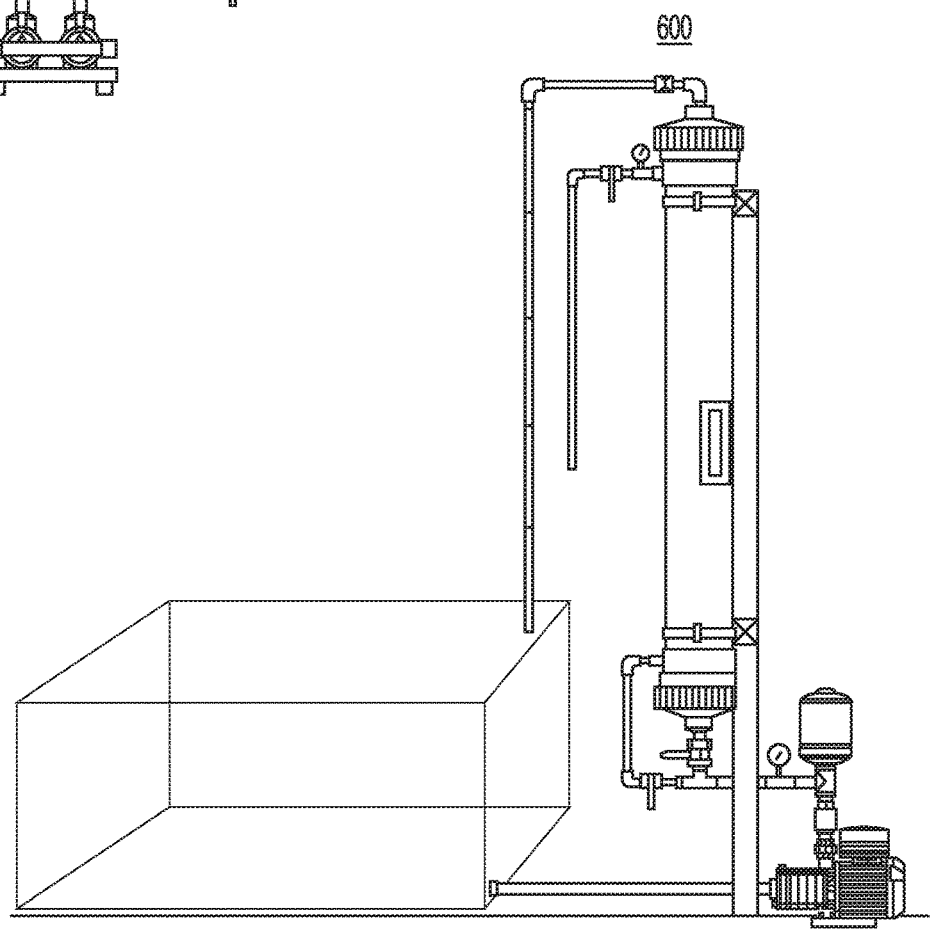
FIG. 25 is a side view of the hollow fiber membrane microalgae harvesting device according to the present invention.
Figure 26:
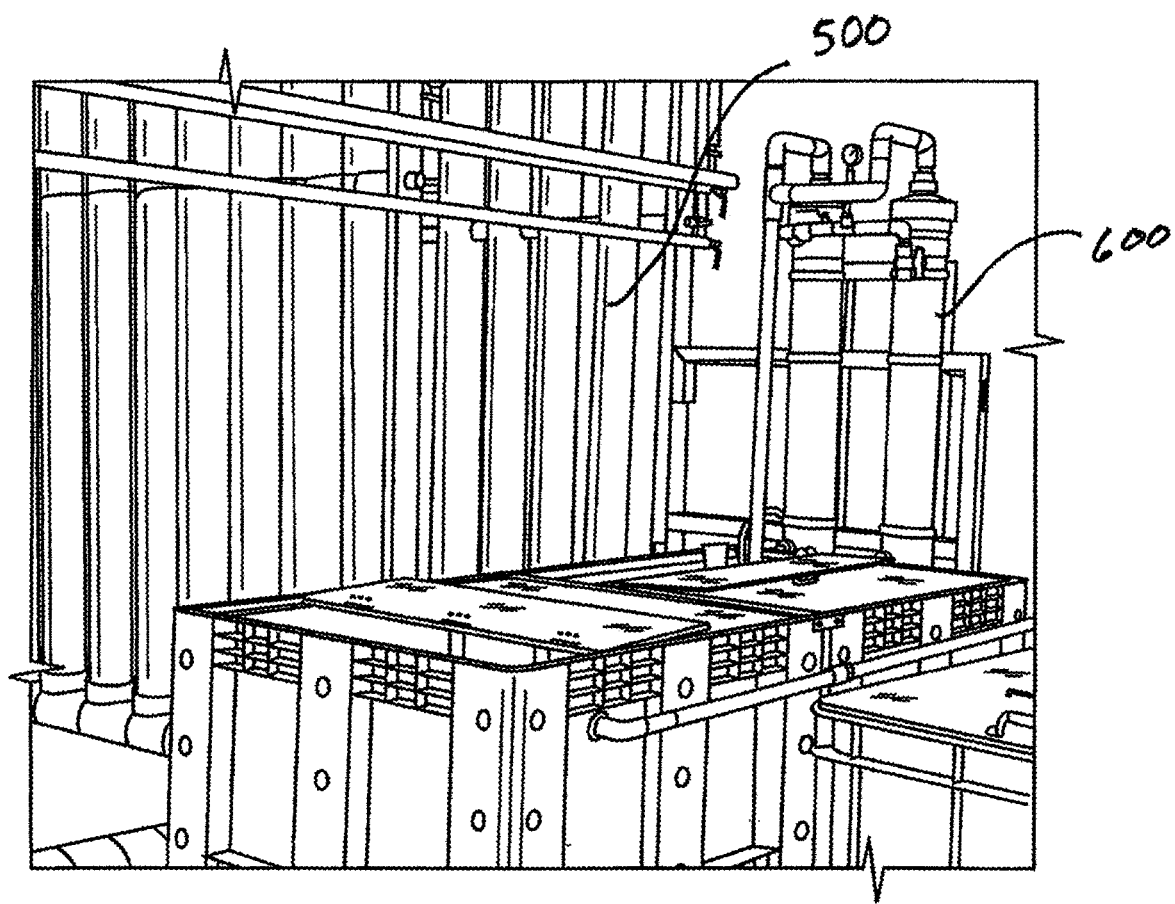
FIG. 26 is an illustration of the hollow fiber membrane microalgae harvesting device installed according to the present invention.

FIG. 24 is a front view of the hollow fiber membrane microalgae harvesting device 600 according to the present invention and FIG. 25 is a side view of the hollow fiber membrane microalgae harvesting device 600 according to the present invention. In general, the hollow fiber membrane microalgae harvesting device 600 concentrates the cultured microalgae by passing the culture past hollow fibers at high pressure. The openings in the fibers are too small for the microalgae to pass through so the micro algae is concentrated. FIG. 26 is an illustration of the hollow fiber membrane microalgae harvesting device 600 installed according to the present invention.

Figure 27:
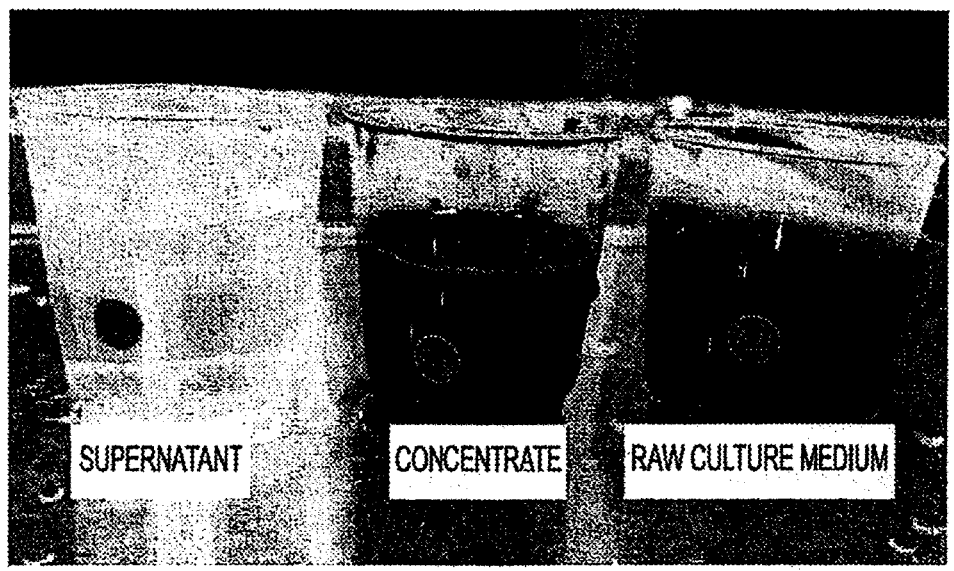
FIG. 27 is a photo of the results of operation of the hollow fiber membrane microalgae harvesting device according to the present invention.

FIG. 27 is a photo of the results of operation of the hollow fiber membrane microalgae harvesting device 600 according to the present invention. As shown in FIG. 27, the raw culture media (far right) is filtered to produce concentrate (middle container) and supernatant (far left).

Figure 28:
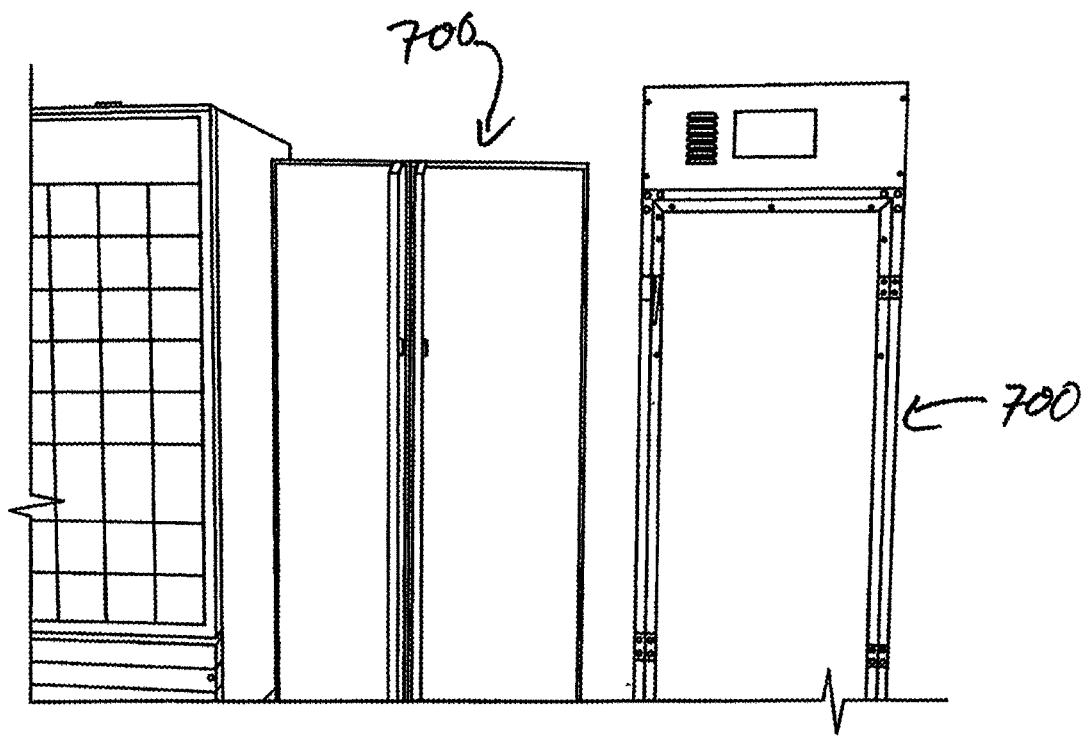
FIG. 28 is an illustration of the microalgae drying device installed according to the present invention.
Figure 29:
FIG. 29 is a photo of the inside of the microalgae drying device installed according to the present invention after drying.
Figure 30:
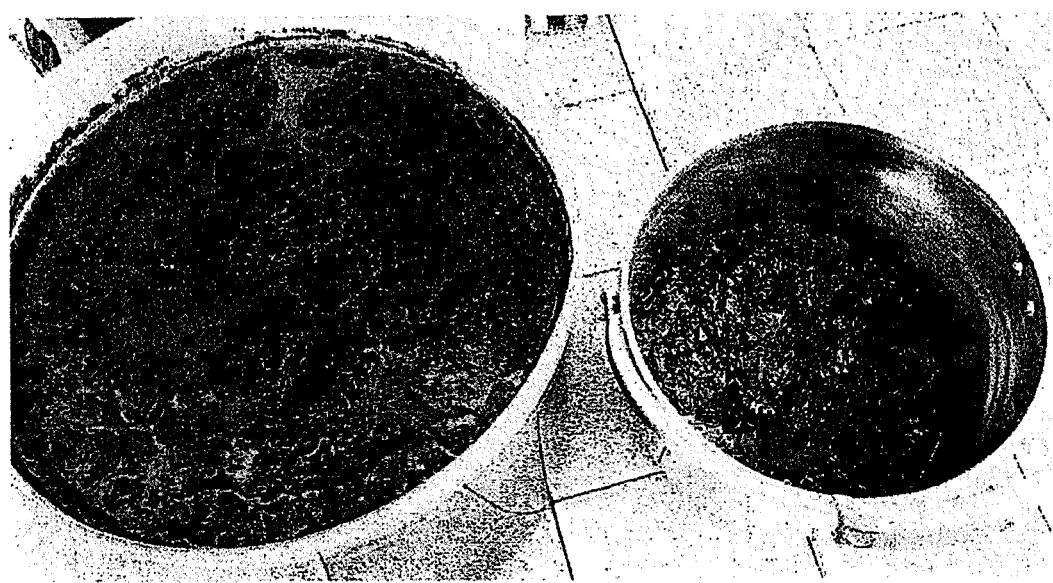
FIG. 30 shows photos of the microalgae drying device according to the present invention prior to and after (right side) drying.
Figure 31:
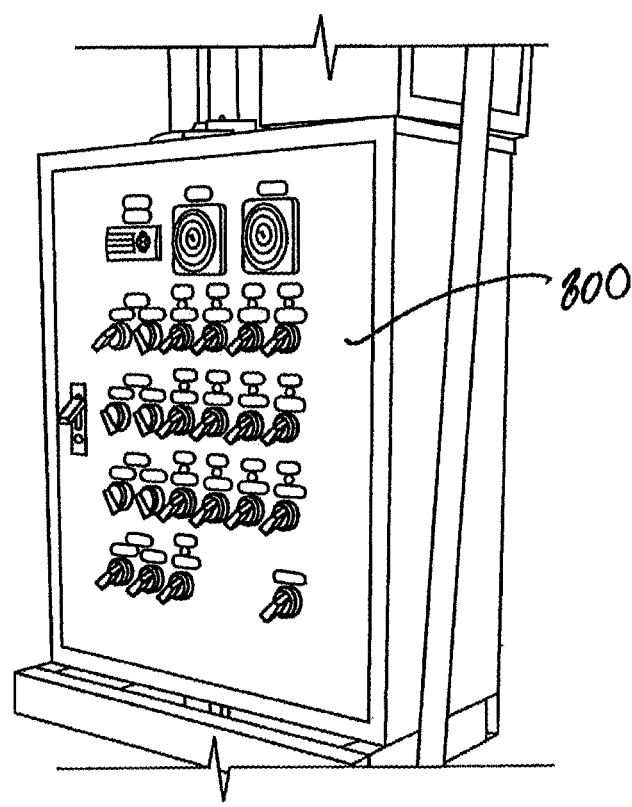
FIG. 31 is an illustration of the automatic control system for the greenhouse installed according to the present invention.

FIG. 28 is an illustration of the microalgae drying device 700 installed according to the present invention. FIG. 29 is a photo of the inside of the microalgae drying device 700 installed according to the present invention after drying. FIG. 30 shows photos of the concentrated microalgae before (left bucket) and after (right bucket) drying in the microalgae drying device 700 according to the present invention. FIG. 31 is an illustration of the automatic control system 800 for the greenhouse 101 installed according to the present invention.

In the following, an embodiment of the present invention is described with reference to the exemplary embodiments thereof. The embodiments represent the results of a 1-month test run of the present invention. The embodiments contained herein are exemplary embodiments of the present invention, and it shall be obvious to a person having ordinary skill in the art that these embodiments are not intended to restrict the protective scope of the present invention to these embodiments.

EXAMPLES

In the present experiment, the cold water marine microalgae *Nannochloropsis* sp. was used in an outdoor growth experiment with 2 tons of culture broth for the purpose of evaluating the productivity of the high-efficiency vertical photobioreactor invented by the present inventor. In the experiment, which was carried out for 1 month, average daily productivity was 0.953 g/L in the culture with 0.1% $CO_2$ introduced, while productivity was 0.574 g/L when only air was introduced. As for temperature distribution, the range was from a minimum of 20° C. to a maximum of 31° C. It was shown that there was no significant difference in productivity according to temperature within this range. Light was shone at a brightness of 5,000 to 40,000 Lux, and it was found that the intensity of the light and the growth of the microalgae were very closely related. Meanwhile, it was found that the method of microalgae culturing by pressurized in-reactor flotation attempted in the present experiment was highly effective.

The strain used in the present experiment was *Nannochloropsis* sp. (KMMCC-290) from the Korean Marine Microalgae Culture Center, and CONYWY culture base was used to culture the strain (Cuillard and Ryther, 1962). The strain was liquid and solid cultured under 25° C. temperature conditions, and was stored or used for inoculation.

The basic composition of the experimental device for outdoor culture testing is as follows: photobioreactors, air compressor, carbon dioxide injector, culture broth mixer and culture broth harvester shown in FIG. 21. The photobioreactors were connected to a special transparent polycarbonate pipe 4,000 mm long with a diameter of 140 mm, with 20 photobioreactors attached to each of 2 lines. 2,000 L seawater sterilized using the micro bubble device ($OH^-$) was injected. Each line was inoculated with 200 L, which is 1/10 of the 2,000 L total amount of culture broth, to a concentration of about $5.0 \times 10^7$ cells per mL. Eight (8) hours after inoculation, sterilized cow's urine as a source of nitrogen and other inorganic nutrients was injected to a concentration of 0.5%, and culturing was continued. In one line, air (including 0.03% carbon dioxide) was supplied through the air compressor, and in the other line, 0.1% liquefied carbon dioxide was mixed in.

The inoculated culture broth was cultured for the first 5 days after inoculation in an optimized state with the air compressor valve was adjusted so that the culture broth would not reach the connecting PVC pipes attached to the top of each culture pipe. On the sixth day, 50% or 1,000 L of the culture broth was discharged through the lower pipes, and harvested. Then each line was replenished with 500 L of new culture broth, an amount equivalent to the culture broth discharged from each. This was repeated every 24 hours, with the photobioreactors operated continuously for 30 days.

The 1,000 L of harvested high-concentration culture broth was further concentrated using a hollow fiber membrane, and after about 30 minutes, the concentrated microalgae was desalinated 2 times with fresh water. The desalinated microalgae was dried using an oven dryer to a moisture content of 4% of less, after which the total dry cell weight was found to determine the total cell mass.

A certain amount of the specimens collected from each of the culture broths was diluted, and the cell count was measured using a hemocytometer. The measured cell count was divided by the cell mass to give the dry cell weight per cell. Note that intensity of illumination during culturing was measured using a portable Lux meter capable of measuring between 600 and 300,000 Lux. Units are shown in Lux.

As shown in FIG. 22, the number of cells prior to addition to inorganic nutrients in the line (Line A) injected with air only and the line injected with a mixture of air and 0.1% carbon dioxide (Line B) was found to be 0.55 to $0.60 \times 10^7$ cells indicating a suitable initial dilution rate. From the second day after inoculation until harvesting, the cell count approximately doubled in both lines, reaching $2.6 \times 10^7$ cells and $4.8 \times 10^7$ cells, respectively, on the 5th day after inoculation, one day prior to harvesting. As was expected, the growth rate of the cells in Line B with the injected carbon dioxide was higher than in Line A. The pre-harvest cell count of Line B was almost double that of Line A.

Harvesting of cells was attempted from the 6th day after inoculation onward. It was determined that the culture broth would be extracted at this time based on results from previous experiments wherein the peak exponential growth rate was reached between 120 and 150 hours. Accordingly, the culture broth was extracted every 24 hours for harvesting from the 6th day onward. The amount of culture broth extracted at this point was 1,000 L, or 50% of the 2,000 L total. This was because the optimal culture state was reached 24 hours after replenishment with new culture broth immediately following 50% extraction. The concentration of cells within the photobioreactors immediately prior to extraction on the 6th day was $3.5 \times 10^7$ cells and 6 $0.1 \times 10^7$ cells per 1 ml for Line A and Line B, respectively.

After initial inoculation, 1,000 L of culture broth was extracted from the 6th day onward, on which it was judged that the peak of the exponential growth phase was reached. As shown in FIG. 23, culturing continued for an additional 25 days, replenishing the photobioreactors with the same amount of culture broth extracted. To analyze the growth rate, the cell counts were measured in the culture broth immediately after inoculation and immediately prior to extraction. By finding the cell count and dry cell weight of the extracted microalgae, the average daily cell count and growth rate, etc., were analyzed as shown in FIG. 23 and Table 1.

TABLE 1

Specific Growth Rate, Average Cell Number, and Average Dry Weight of Cells in A & B Lines.

|  | Average cell number per day | Average dry cell weight per day | Specific growth rate (k) |
|---|---|---|---|
| A Line | $3.83 \times 10^7$ cells/ml | 0.574 g/L | 0.047 |
| B Line | $6.35 \times 10^7$ cells/ml | 0.953 g/L | 0.055 |

For Line B, with 0.1% $CO_2$ injected, the daily average cell count per 1 ml immediately prior to extraction was found by dividing the total cell count over 25 days, giving a value of $6.35 \times 10^7$ cells/ml. Meanwhile, the growth rate inside the photobioreactors was found using the following equation, which applies to the growth rate of cells in the exponential growth phase.

In the equation for cell growth rate: $N=No2n$, N it the cell count after t hours have passed, and N0 is the initial cell count. The lower case n is the number of generations within t hours. Substituting Log functions in the equation above gives the following: Log N=Log N0+n Log 2. The total generation count, n, becomes Log N−Log N0÷Log 2 (0.301). Here, the initial cell count N0 is the total cell count within the 2-ton photobioreactor which has been replenished with an equal amount of new culture broth after 100 L of high-concentration pressurized flotation culture broth has been extracted. The cell count N after 5 hours becomes the total cell count when 24 hours have passed after the addition of culture broth, immediately prior to extraction.

In Line B, the initial cell count and the total cell count immediately prior to extraction are as follow, and accordingly, the total number of generations, n, becomes approximately 4.40 generations. Where the initial cell count $N0=3.0 \times 10^6$ cells/ml. The cell count immediately prior to harvesting $N=6.35 \times 10^7$ cells/ml. The total generation count n=Log N−Log N0÷0.301≈4.40

Meanwhile, the specific growth rate of cells, k, was found to have a value of 0.301/g, were g is doubling time. The doubling time is the total culturing time divided by the number of generations. The g value for Line B, which is 24 hours divided by the generation count of 4.4, becomes approximately 5.45 hours. Accordingly, the specific growth rate K for Line B was found to have a value of approximately 0.055, which is 0.301 divided by 5.45 hours. Where g=t/n=24 hours/4.4 generations≈5.45 and where k=0.301/g=0.301/5.45≈0.055.

For Line A, injected with air only, the initial cell count after dilution was measured at $2.8 \times 10^6$ cells/ml, giving a total generation count of approximately 3.77 generations, approximately 6.37 hours' generation time, and a value of 0.047 for the specific growth rate k.

Meanwhile, the average daily dry cell weight for Line B found by drying 100 L of the harvested cells was calculated to be 1,800 g. Diving this by the total cell count gave a dry cell weight of 0.015 μg/cell. Multiplying this by the average daily cell count of $6.35 \times 10^7$ cells/ml×2.000 L gave an average daily cell mass per liter of 0.953 g/L for Line B. The cell mass for Line A, which was not supplied with carbon dioxide, was calculated to be 0.574 g/L.

Figure 32:
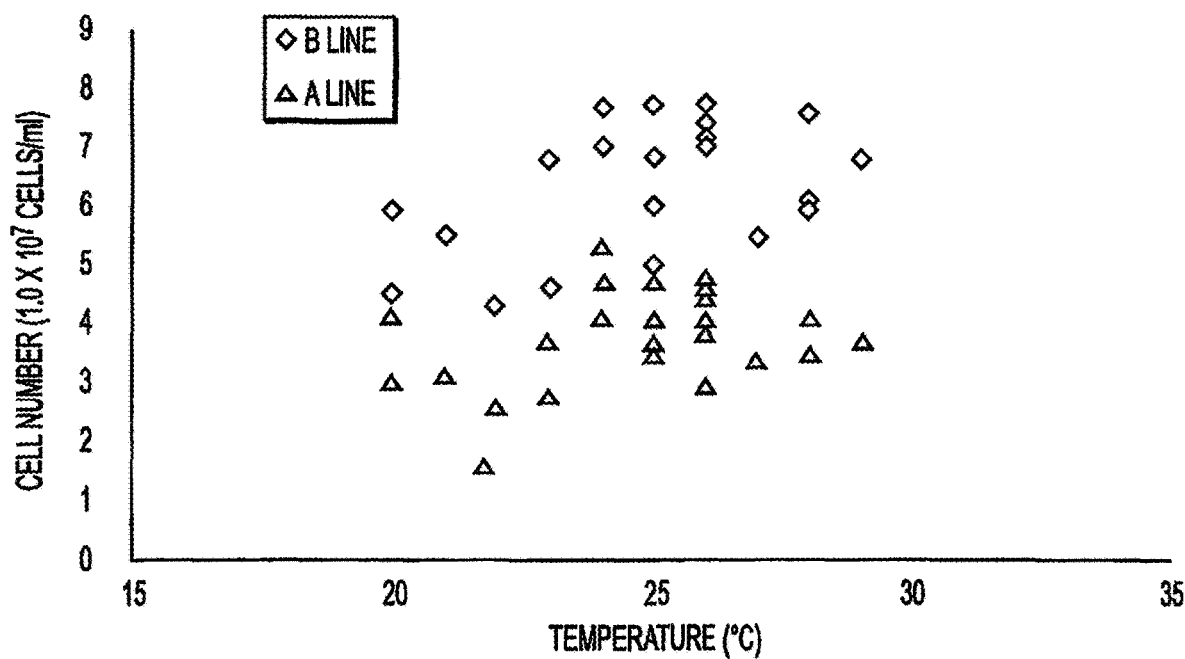
FIG. 32 is a graph showing density of cells as a function of growth temperature according to the present invention.

The present experiment was carried out in Gangneung, S. Korea, over the month of September 2014. The minimum air temperature in the area was around 20° C., with a maximum daytime temperature exceeding 30° C. In order to keep the temperature of the culture broth between 25° C. and 30° C., chilled air was injected when the temperature of the culture broth exceeded 29° C. to regulate the maximum temperature to no more than 30° C. During the experimental period, the culture broth recorded a minimum temperature of 20° C., reaching a maximum temperature of 31° C. As seen in FIG. 32, temperature changes during the experimental period did not have a large impact on cell growth. This is judged to be because the range of temperature variation was small, at 25° C.±5° C.

Among the environmental factors impacting the growth of microalgae, the role of light is very important. The results of the present experiment also gave results demonstrating this influence of light. Around September 2014, when the experiment was carried out, the weather in Gangneung was sunny about half of the time, and cloudy the rest. On rainy or cloudy days, the intensity of illumination was generally between 5,000 and 30,000 Lux, while 300,000 Lux was exceeded during the daytime on sunny days. Excessively intense light can stop photosynthesis due to light saturation, and radiant heat can cause the temperature of the culture broth to increase, suppressing growth of the cold water marine organism *Nannochloropsis* sp. Therefore, a shade was installed on clear days with intense sunlight, keeping light intensity between 20,000 to 30,000 Lux.

Figure 33:
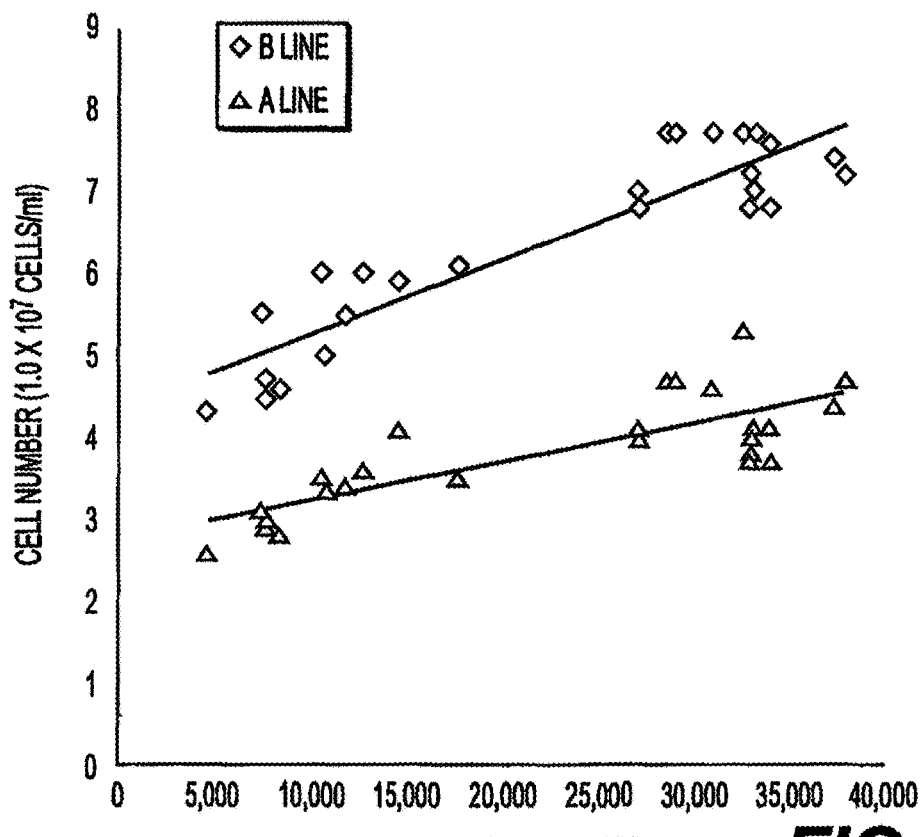
FIG. 33 is a graph showing density of cells as a function of growth illumination according to the present invention.

Observation of microalgae growth from the 6th day after inoculation to the 30th day, when the experiment ended, showed that there was a very close correlation between light intensity and algal growth, as seen in FIG. 33. Also, it can be known that the growth rate had a steeper incline when 0.1% carbon dioxide was injected than when only oxygen was injected.

The hydroxyl radicals (OH—) in the present experiment, which dissolve toxins within the raw culture broth, can be reused. It is expected that the sealed vertical photobioreactor will be an economically feasible, technologically advanced and environmentally friendly system for microalgae culturing and harvesting.

Meanwhile, it was discovered in the present growth rate experiment that light and carbon dioxide acted as key elements of growth, according to which further research will be conducted into the optimum concentration of carbon dioxide for growth and the impact of light intensity and different light wavelengths on growth in order to further improve productivity.

A preferred embodiment of the present invention has been described in detail in the foregoing, and the substantial scope of the present invention will be defined by the appended claims and equivalents thereof.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

PCT/US2017/040760, having an international filing date of Jul. 5, 2017, is incorporated by reference herein in its entirety.

What is claimed is:

1. A method for culturing microalgae, comprising supplying microalgae and air to an apparatus for cultivation of microalgae in a culture broth, the apparatus comprising:
    a device for culture broth sterilization using a micro bubble generator;
    an air compression and pressure equalization device for injection of carbon dioxide and oxygen from atmosphere into a culture broth;
    an air chilling device to maintain suitable culture broth temperature in response to a water temperature being higher than a predetermined maximum temperature;
    an automatic carbon dioxide supply device to promote photosynthesis;
    a sealed vertical photobioreactor configured to contain a culture medium inoculated with a microalgae;
    a harvesting device using hollow fiber membranes; and
    a hot air drying device using the waste heat generated by air compression.

2. The method according to claim 1, wherein the air compression and pressure equalization device comprises a device to compress carbon dioxide and oxygen in atmosphere to 10 bar, a device to equalize air pressure, and pipes and a gas backflow preventing device to inject compressed gases into a culture broth.

3. The method according to claim 1, wherein the automatic carbon dioxide supply device supplies liquefied carbon dioxide into a culture broth using a pH sensor.

4. The method according to claim 3, wherein the automatic carbon dioxide supply device automatically supplies carbon dioxide when pH of a culture broth is 7.26 or higher, and automatically cuts off carbon dioxide when pH of a culture broth is less than 7.26 if the microalgae is a freshwater microalgae, and automatically supplies carbon dioxide when pH of a culture broth is 7.30 or higher, and automatically cuts off carbon dioxide when pH of culture broth is less than 7.30 if the microalgae is a seawater microalgae.

5. The method according to claim 1, wherein compressed gases are injected into bottom of the apparatus.

6. The method according to claim 5, wherein the apparatus further comprises a device for control of gas pressure.

7. The method according to claim 6, wherein mutual exchange and flow of culture broth among identical connected vertical photobioreactors is induced by buoyant force of the device for control of gas pressure.

* * * * *